United States Patent [19]

Kaddurah-Daouk et al.

[11] Patent Number: 6,075,031
[45] Date of Patent: Jun. 13, 2000

[54] USE OF CREATINE ANALOGUES AND CREATINE KINASE MODULATORS FOR THE PREVENTION AND TREATMENT OF GLUCOSE METABOLIC DISORDERS

[75] Inventors: Rima Kaddurah-Daouk, Belmont, Mass.; Beverly A. Teicher, Carmel, Ind.

[73] Assignees: Dana-Farber Cancer Institute, Cambridge; Avicena Group, Inc., Boston, both of Mass.

[21] Appl. No.: 08/914,887

[22] Filed: Aug. 19, 1997

Related U.S. Application Data

[63] Continuation-in-part of application No. 08/540,894, Oct. 11, 1995.
[51] Int. Cl.[7] ..................... A61K 31/505; A61K 31/415; A61K 31/295; A61K 31/185
[52] U.S. Cl. ........................ 514/275; 514/385; 514/386; 514/396; 514/501; 514/553; 514/563; 514/564; 514/565; 514/579; 514/631; 514/646
[58] Field of Search ................................. 514/275, 385, 514/386, 396, 553, 501, 563, 564, 565, 579, 631, 646

[56] References Cited

U.S. PATENT DOCUMENTS

| | | | |
|---|---|---|---|
| 5,077,313 | 12/1991 | Lubec | 514/565 |
| 5,091,404 | 2/1992 | Elgebaly | 514/401 |
| 5,321,030 | 6/1994 | Kaddurah-Daouk et al. | 514/275 |
| 5,324,731 | 6/1994 | Kaddurah-Daouk et al. | 514/275 |

FOREIGN PATENT DOCUMENTS

| | | |
|---|---|---|
| 891509 | 1/1972 | Canada . |
| 1153424 | 4/1965 | United Kingdom . |
| 1195199 | 11/1966 | United Kingdom . |
| 1195200 | 2/1967 | United Kingdom . |
| 1552179 | 11/1976 | United Kingdom . |
| WO 90/09192 | 8/1990 | WIPO . |
| WO 91/12799 | 9/1991 | WIPO . |
| WO 92/08456 | 5/1992 | WIPO . |
| WO 94/16687 | 8/1994 | WIPO . |

OTHER PUBLICATIONS

Rocic et al., "Hypoglycemic effect of creatine in insulin dependent diabetic patients" (1995).

Kaddurah–Daouk et al., "Inhibiting undesirable cell growth–by adminstering of creatine cpd and hyperplastic inhibitory agent" (1995).

Gullans et al., "Treatment of osmotic disturbance in animal by adminstering organic osmolyte." (1991).

Windolz et al., The Merck Index, Tenth Edition (1983) p. 723, abstract No. 4886.

Annesley, T. and Walker, J., "Cyclocreatine Phosphate as a Substitute for Creatine Phosphate in Vertebrate Tissue. Energetic Considerations," *Biochem. Biophys. Res. Commun.*, vol. 74, 185–90 (1977).

Aynsley–Green, A. and Alberti, K.G.M.M., "In Vivo Stimulation of Insulin Secretion by Guandine Derivatives in the Rat," *Horm. Metab. Res.*, vol. 6, 115–20 (1974).

Buckle, A.L.J. and Jones, H.E.H., "Pharmacological Studies on γ–Guanidinobutyramide," *Horm. Metab. Res.*, vol. 3, 76–81 (1971).

Cramer, F. et al., "Die Synthese der Argininphosphorsäure und die Reaktion von Isoureidophosphonaten mit Aminen," *Chem. Ber.*, vol. 95, 1670–82 (1962).

Griffiths, G. and Walker, J., "Accumulation of Analog of Phosphocreatine in Muscle of Chicks Fed 1–Carboxymethyl–2–iminoimidazolidine (Cyclocreatine)," *J. Biol. Chem.*, vol. 251, No. 7, 2049–54 (1976).

Lowe, G. and Sproat, B., "Evidence for an Associative Mechanism in the Phosphoryl Transfer Step Catalyzed by Rabbit Muscle Creatine Kinase," *J. Biol. Chem.*, vol. 225, No. 9, 3944–51 (1980).

Malaisse, W.J. et al., "Metabolic Effects of γ–Guanidinobutyramide. I. In Vivo Study in Anesthetized Dogs," *Horm. Metab. Res.*, vol. 1, 258–65 (1969).

McLaughlin, A. and Cohn, M., "Specificity of Creatine Kinase for Guanidino Substrates," *J. Biol. Chem.*, vol. 247, No. 13, 4382–8 (1972).

Moerland, T.S. et al., "Administration of a Creatine Analogue Induces Isomyosin Transitions in Muscle," *Am. J. Physiol.*, vol. 257, C810–6 (1989).

Roberts, J. and Walker, J., "Higher Homolog and N–Ethyl Analog of Creatine as Synthetic Phosphagen Precursors in Brain, Heart, and Muscle, Repressors of Liver Amidinotransferase, and Substrates for Creatine Catabolic Enzymes," *J. Biol. Chem.*, vol. 260, No. 25, 13502–8 (1985).

Roberts, J. and Walker, J., "Synthesis and Accumulation of an Extremely Stable High–Energy Phosphate Compound by Muscle, Heart, and Brain of Animals Fed the Creatine Analog, 1–Carboxyethyl–2–iminoimidazolidine (Homocyclocreatine)," *Arch. Biochem. Biophys.*, vol. 220, No. 2, 563–71 (1983).

(List continued on next page.)

*Primary Examiner*—Kevin E. Weddington
*Attorney, Agent, or Firm*—Lahive & Cockfield, LLP; Elizabeth A. Hanley, Esq.

[57] ABSTRACT

The present invention relates to the use of creatine compounds including cyclocreatine and creatine phosphate for treating or preventing a metabolic disorder consisting of hyperglycemia, insulin dependent diabetes mellitus, impaired glucose tolerance, hyperinsulinemia, insulin insensitivity, diabetes related diseases in a patient experiencing said disorder. The creatine compounds which can be used in the present method include (1) analogues of creatine which can act as substrates or substrate analogues for the enzyme creatine kinase; (2) compounds which can act as activators or inhibitors of creatine kinase; (3) compounds which can modulate the creatine transporter (4) N-phosphocreatine analogues bearing transferable or non-transferable moieties which mimic the N-phosphoryl group. (5) compounds which modify the association of creatine kinase with other cellular components.

15 Claims, 15 Drawing Sheets

OTHER PUBLICATIONS

Rowley, G.L. et al., "On the Specificity of Creatine Kinase. New Glycocyamines and Glycocyamine Analogs Related to Creatine," *Journal of the American Chemical Society*, vol. 93, 5542–51 (1971).

Schafer, G., "Biguanides: A Review of History, Pharmacodynamics and Therapy," *Diabete & Metabolisme* (Paris), vol. 9, 148–63 (1983).

Teicher, B. et al., "Cyclocreatine in Cancer Chemotherapy," *Cancer Chemother. Pharmacol.*, vol. 35, 411–6 (1995).

Wallimann, T. et al., "Intracellular Compartmentation, Structure and Function of Creatine Kinase Isoenzymes in Tissues with High and Fluctuating Energy Demands: The 'Phosphocreatine Circuit' for Cellular Energy Homeostasis," *Biochem. J.*, vol. 281, 21–40 (1992).

Watanabe, C.K., "Studies in the Metabolic Changes Induced by Administration of Guanidine Bases. I. Influence of Injected Guanidine Hydrochloride Upon Blood Sugar Content," *J. Biol. Chem.*, vol. 33, 253–65.

USE OF CREATINE ANALOGUES AND CREATINE KINASE MODULATORS FOR THE PREVENTION AND TREATMENT OF GLUCOSE METABOLIC DISORDERS

RELATED APPLICATIONS

The present invention is a continuation-in-part of Ser. No. 08/540,894, filed Oct. 11, 1995, the entire disclosure of which is incorporated herein by reference.

FIELD OF INVENTION

The present invention provides for new use for creatine compounds (compounds which modulate one or more of the structural or functional components of the creatine kinase/creatine phosphate system) as therapeutic agents. More particularly, the present invention provides a method of treating or preventing certain metabolic disorders of human and animal metabolism, e.g., hyperglycemia, insulin dependent diabetes mellitus, impaired glucose tolerance, insulin insensitivity, hyperinsulinemia and related diseases secondary to diabetes.

BACKGROUND OF THE INVENTION

There are several metabolic diseases of human and animal glucose metabolism, eg., hyperglycemia, insulin dependent diabetes mellitus, impaired glucose tolerance, hyperinsulinemia, and insulin insensitivity, such as in non-insulin dependent diabetes mellitus (NIDDM). Hyperglycemia is a condition where the blood glucose level is above the normal level in the fasting state, following ingestion of a meal or during a glucose tolerance test. It can occur in NIDDM as well as in obesity. Hyperglycemia can occur without a diagnosis of NIDDM. This condition is called impaired glucose tolerance or pre-diabetes. Impaired glucose tolerance occurs when the rate of metabolic clearance of glucose from the blood is less than that commonly occurring in the general population after a standard dose of glucose has been orally or parenterally administered. It can occur in NIDDM as well as obesity, pre-diabetes and gestational diabetes. Hyperinsulinemia is defined as having a blood insulin level that is above normal level in fasting state or following ingestion of a meal. It can be associated with or causative of hypertension or atherosclerosis. Insulin insensitivity, or insulin resistance occurs when the insulin-dependent glucose clearance rate is less than that commonly occurring in the general population during diagnostic procedures.

A number of compounds have been tried to alleviate symptoms associated with glucose metabolism disorders. For example, guanidine, monoguanidine and biguanidine compounds have been shown to produce hypoglycemia. Watanabe, C., *J. Biol. Chem.,* 33:253–265 (1918); Bischoff, F. et al., *Guanidine Structures and Hypoglycemia,* 81:325–349 (1929). However these compounds were shown to be toxic. Biguanide derivatives, e.g., phenformin and metformin, have been used clinically as antidiabetic agents. Some members of this class continue to be used today, while others have been withdrawn from the market. Schafer, G., *Diabetes Metabol. (Paris)* 9:148–163 (1983). Gamma-guanidinobutyramide, also known as Tyformin, and its salt derivative, Augmentin, were investigated as potential antidiabetic agents from the mid 1960's to mid 1970's. While Augmentin produced hypoglycemia, it was reported to have major undesirable side effects such as hypertension and circulatory collapse. Malaisse, W. et al., *Horm. Metab. Res.,* 1:258–265 (1969); ibid, 3:76–81 (1971).

British patent 1,153,424 discloses the use of certain esters and amides of guanidino-aliphatic acids in the treatment of diabetes mellitus where hyperuremia is present. The patent does not disclose that these compounds have an effect on hyperglycemia or any other symptom or pathological state related to disease. Canadian patent 891509 discloses the use of esters and amides of guanidinoaliphatic acids were disclosed for treating hyperuremia and hyperglycemia in diabetes mellitus.

British patents 1,195,199, and 1,195,200 disclose the use of guanidino alkanoic acids or their amides or esters for the treatment of hyperglycemia occurring in diabetes. A variety of British patents (1,552,179/1,195,199/1,195,200/1,552,179) describe the low potency of the guanidino alkanoic acid derivatives as single agents but describe their use in combination with other modalities.

Aynsley-Green and Alberti injected rats intravenously with beta guanidino propionic acid, arginine, guanidine, 4 guanidinobutyramide and 4 guanidinobutyric acid. Arginine and beta guanidino propionic acid stimulated insulin release but did not affect glucose levels. Also the treatment of animals with large amounts of beta gunidino propionic acid for several weeks was shown not to affect glucose levels, Moerland, T. et al., *Am. J. Physiol.,* 257:C810–C816 (1989). Under different conditions beta gunidino propionic acid was shown to have an effect as described later. The two other compounds did stimulate insulin release but increased glucose levels. Aynsley-Green, A. et al., *Horm. Metab.,* 6:115–120 (1974).

It is an object of the present invention to provide methods for treatment of metabolic diseases that relate to glucose level regulation by administering to an afflicted individual an amount of a compound or compounds which modulate one or more of the structural or functional components of the creatine kinase/creatine phosphate system sufficient to prevent, reduce or ameliorate the symptoms of the disease. These compounds are collectively referred to as "creatine compounds." The experiments described herein demonstrate that the creatine kinase system is directly related to control of blood glucose levels in animals. Creatine analogues are shown herein to be effective hypoglycemic agents for treatment of glucose metabolic diseases.

SUMMARY OF THE INVENTION

The present invention provides a method of treating or preventing a glucose metabolic disorder using creatine, creatine phosphate, or a compound or compounds which modulates one or more of the structural or functional components of the creatine kinase/creatine phosphate system. Disorders which may be treated using the present invention include, for example, those selected from the group consisting of hyperglycemia, insulin dependent diabetes mellitus, impaired glucose tolerance, hyperinsulinemia and diabetes related complications. The method of the invention comprises administering to a subject afflicted with or susceptible to said disorder an amount of a creatine compound (compounds which modulate one or more of the structural or functional components of the creatine kinase/creatine phosphate system) sufficient to alleviate or prevent the symptoms of the disorder. The creatine compound may be in the form of a pharmacologically acceptable salt or combined with an adjuvant or other pharmaceutical agent effective to treat or prevent the disease or condition.

Prior to the present invention, the creatine kinase system had not been implicated in glucose metabolic disorders. The substrates for the creatine kinase enzyme, i.e., creatine and creatine phosphate, are both guanidino compounds. The present inventors have discovered that the creatine kinase (CK) enzyme modifies key events involved in glucose regulation by potentially regulating energy (ATP) involved in the release of insulin or the uptake of glucose in tissue. It is now possible to modify the CK system and design compounds that can prevent or ameliorate these diseases. The present invention demonstrates that at least two creatine compounds, creatine phosphate and cyclocreatine, are hypoglycemic agents. That is, these compounds cause glucose levels to drop significantly in a subject.

As stated herein above, a variety of guanidino compounds have been shown to act as hypoglycemic agents including the compound beta guanidino propionic acid (see, for example, PCT Publication Number WO 91/12799). The target for these compounds and their mode of action is not fully understood. However, beta guanidino propionic acid was shown not to affect glucose levels in normal animals, but had an effect on glucose levels in a model for non-insulin dependent diabetes mellitus. This compound has some structural similarity to creatine, but does not form a part of this invention. Compounds useful in the present invention are creatine compounds which modulate the creatine kinase system.

The present invention also provides pharmaceutical compositions containing creatine compounds in combination with a pharmaceutically acceptable carrier. The present compositions may be used in combination with effective amounts of standard chemotherapeutic agents which act on regulating glucose levels, such as insulin or sulphonylureas, to prophylactically and/or therapeutically treat a subject with a disease related to glucose levels.

Packaged drugs for treating subjects having a disease relating to glucose level regulation also are the subject of the present invention. The packaged drugs include a container holding the creatine compound, in combination with a pharmaceutically acceptable carrier, along with instructions for administering the same for the purpose of preventing, ameliorating, arresting or eliminating a disease related to glucose level regulation.

By treatment is meant the amelioration of one or more symptoms of, or total avoidance of, the metabolic disorder as described herein. By prevention is meant the avoidance of a currently recognized disease state, as described herein, in a patient evidencing some or all of the glucose metabolic disorders described above. The present compositions may be administered in a sustained release formulation. By sustained release is meant a formulation in which the drug becomes biologically available to the patient at a measured rate over a prolonged period. Such compositions are well known in the art.

DETAILED DESCRIPTION OF THE INVENTION

Figure 1A:
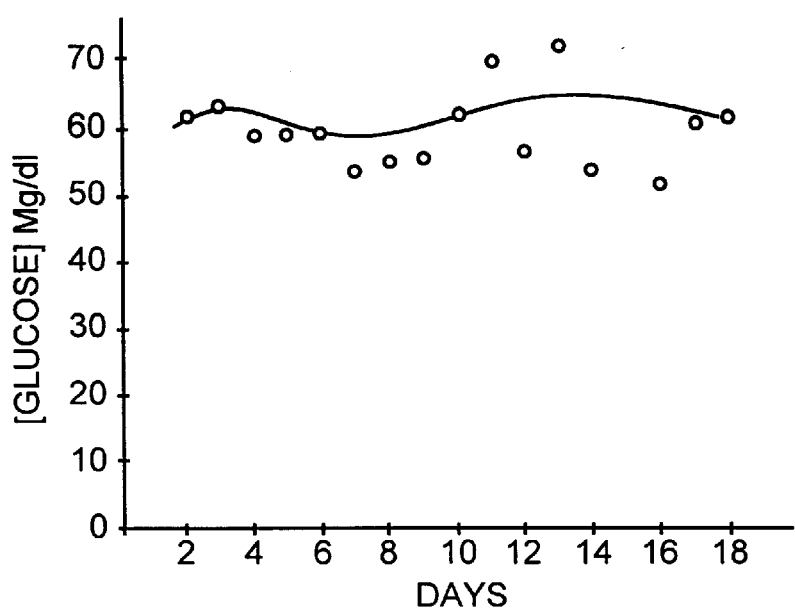
FIG. 1 graphically illustrates the effect of selected creatine compounds on glucose levels in rats: Panel (A): glucose levels in control (unmanipulated animals); Panel (B): glucose levels in cyclocreatine treated animals; Panel (C): glucose levels in beta-guanidino propionic acid treated animals; and Panel (D): glucose levels in creatine phosphate treated animals.
Figure 1B:
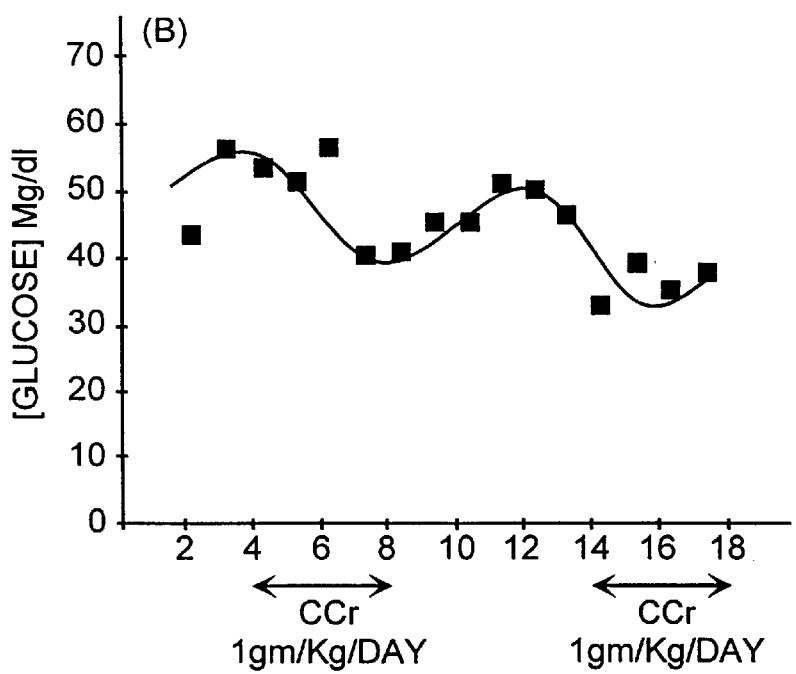
Figure 1C:
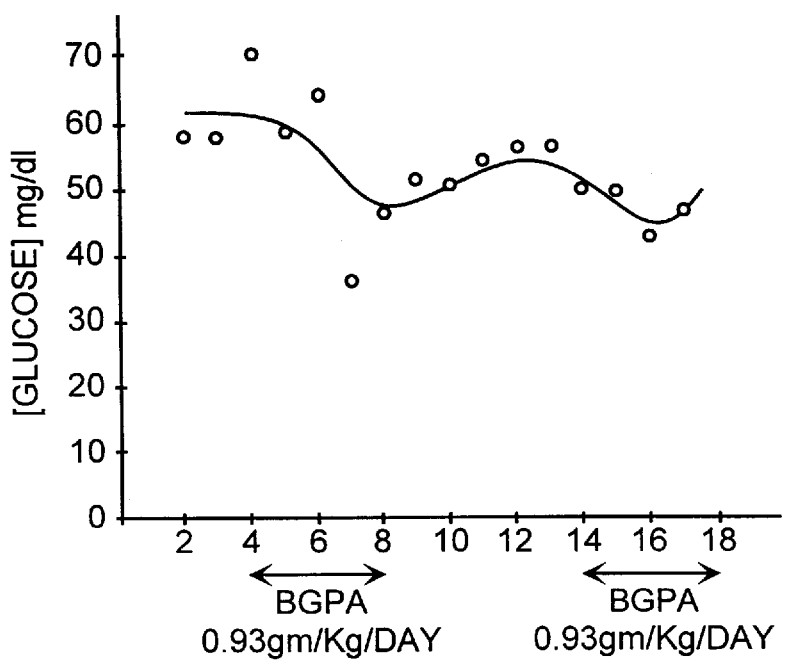
Figure 1D:
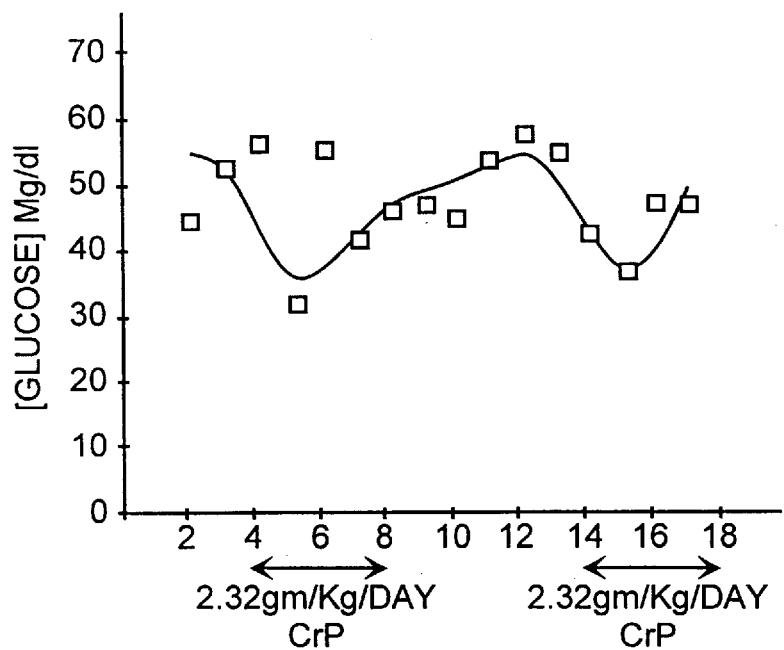
Figure 2A:
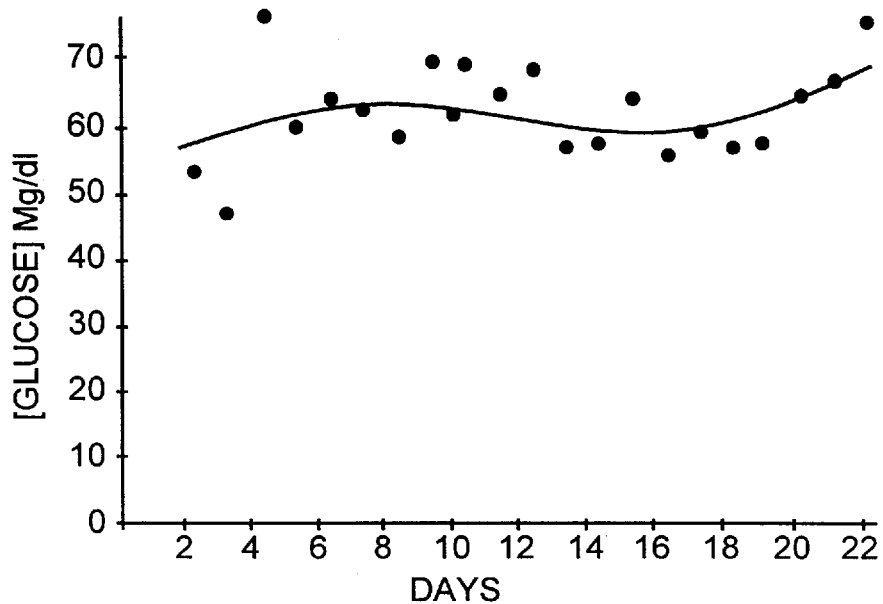
FIG. 2 graphically illustrates the effect of the selected compounds on glucose levels in rats: Panel (A): control (unmanipulated animals); Panel (B): cyclocreatine treated; Panel (C): beta-guanidino propionic acid treated; Panel (D): creatine phosphate treated animals.
Figure 2B:
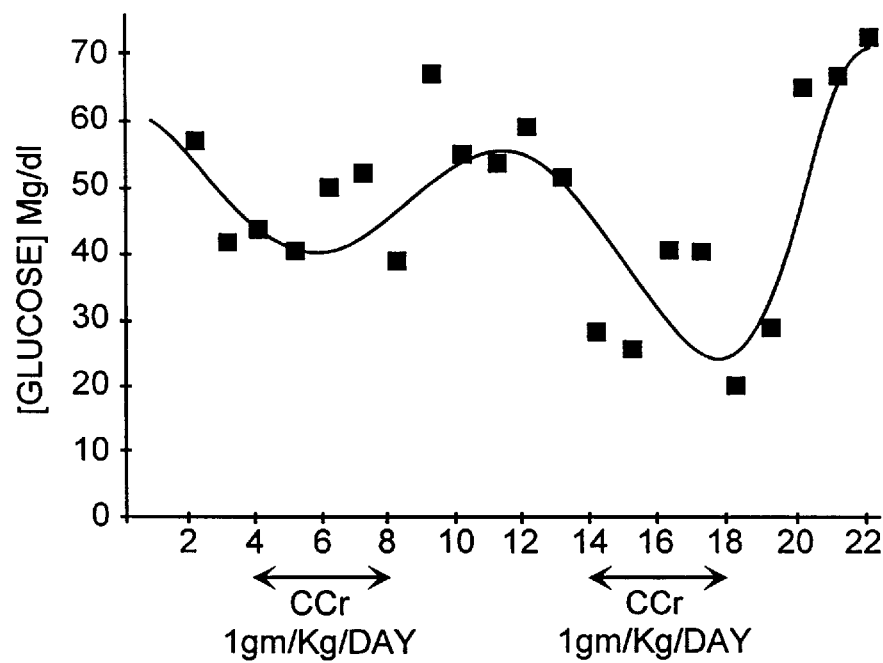
Figure 2C:
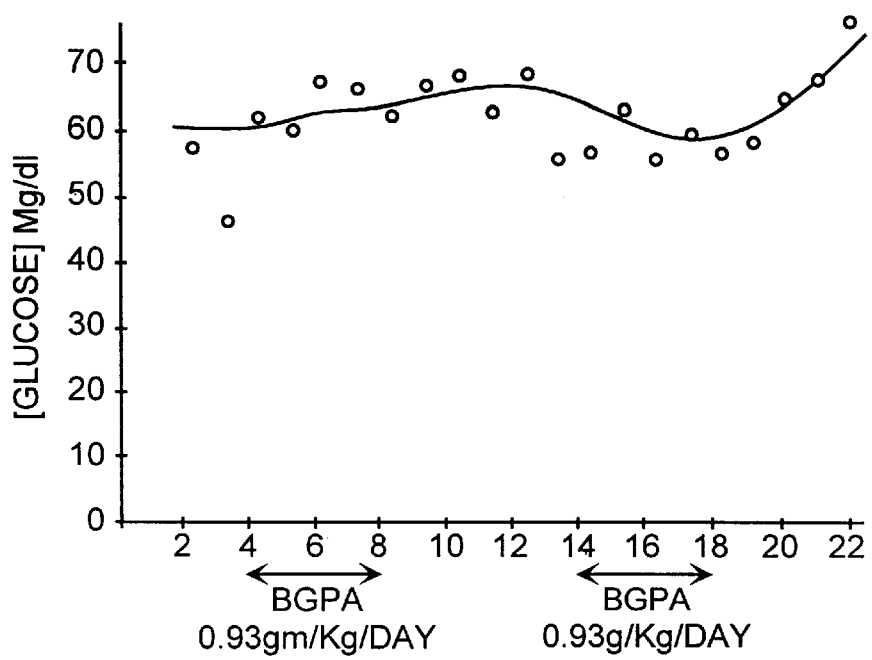
Figure 2D:
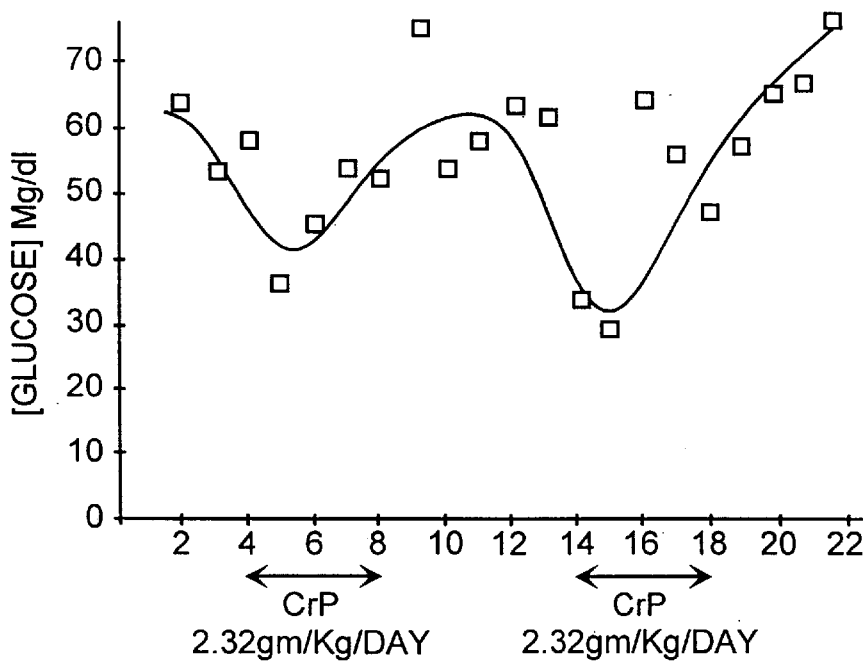

The method of the present invention generally comprises administering to an individual afflicted with a disease or susceptible to a disease involving glucose level regulation, an amount of a compound or compounds which modulate one or more of the structural or functional components of the creatine kinase/phosphocreatine (CK/CrP) system sufficient to prevent, reduce or ameliorate symptoms of the disease. Components of the CK/CrP system which can be modulated include the enzyme creatine kinase (CK), the substrates creatine, creatine phosphate, ADP, ATP, and the transporter of creatine. As used herein, the term "modulate" means to change, affect or interfere with the functioning of the component in the CK/CrP enzyme system.

The CK/CrP is an energy generating system operative predominantly in the brain, muscle, heart, retina, and the pancreas. Wallimann et. al. , Biochem. J., 281, 21–401 (1992). The components of the system include the enzyme creatine kinase (CK), the substrates creatine (Cr), creatine phosphate (CrP), ATP, ADP, and the creatine trasporter. The enzyme reversibly catalyzes the transfer of a phosphoryl group from CrP to ADP to generate ATP. It is found to be localized at sites where rapid rate of ATP replenishment is needed. Some of the functions associated with this system include efficient regeneration of energy in the form of ATP in cells with fluctuating and high energy demand, energy transport to different parts of the cell, phosphoryl transfer activity, ion transport regulation, and involvement in signal transduction pathways.

The substrate creatine is a compound which is naturally occurring and is found in mammalian brain, skeletal muscle, retina and the heart. It's phosphorylated form CrP is also found in the same organs and is the product of the CK reaction. Both compounds can be easily synthesized and are believed to be non-toxic to man. A series of creatine analogues have also been synthesized and used as probes to study the active site of the enzyme. Kaddurah-Daouk et al. (WO 92/08456 published May 29, 1992 and WO 90/09192, published Aug. 23, 1990; U.S. Pat. Nos. 5,321,030; and 5,324,731, the entire disclosures of which are hereby incorporated herein by reference) described methods for inhibiting growth, transformation, or metastasis of mammalian cells using related compounds. Examples of such compounds include cyclocreatine, homocyclocreatine and beta guanidino propionic acid. These same inventors have also demonstrated the efficacy of such compounds for combating viral infections (U.S. Pat. No. 5,321,030). Elgebaly in U.S. Pat. No. 5,091,404 discloses the use of cyclocreatine for restoring functionality in muscle tissue. Cohn in PCT publication No. WO94/16687 describes a method for inhibiting the growth of several tumors using creatine and related compounds. No prior work has established a direct link between the creatine kinase system and diseases related to glucose level regulation such as hyperglycemia, insulin dependent or independent diabetes and related diseases secondary to diabetes.

Compounds which are particularly effective for use in the present invention include cyclocreatine, creatine phosphate and analogues thereof which are described below. The term "creatine compound" will be used herein to include Cr, CrP, cyclocreatine, compounds which are structurally similar to Cr, CrP, and cyclocreatine, and analogues of Cr, CrP, and cyclocreatine. The term "creatine compound" also includes compounds which "mimic" the activity of cyclocreatine and creatine phosphate or creatine analogues i.e., compounds which modulate the creatine kinase system. The term "mimics" is intended to include compounds which may not be structurally similar to creatine but mimic the therapeutic activity of the creatine analogues cyclocreatine and creatine phosphate or structurally similar compounds. The term creatine compounds will also include inhibitors of creatine kinase, ie. compounds which inhibit the activity of the enzyme creatine kinase, molecules that inhibit the creatine transporter or molecules that inhibit the binding of the enzyme to other structural proteins or enzymes or lipids. The term "modulators" of the creatine kinase system" are compounds which modulate the activity of the enzyme, or the activity of the transporter of creatine, or the ability of the enzyme to associate with other cellular components. These could be substrates for the enzyme and they would have the ability to build in their phosphorylated state intracellularly. These types of molecules are also included in our term creatine compounds. The term creatine "analogue" is intended to include compounds which are structurally similar to creatine such as cyclocreatine and creatine phosphate, compounds which are art-recognized as being analogues of creatine, and/or compounds which share the same function as cyclocreatine and creatine phosphate.

Creatine (also known as N-(aminoiminomethyl)-N-methyl glycine; methylglycosamine or N-methyl-guanidino acetic acid) is a well-known substance. See, *The Merck Index*, Eleventh Edition No. 2570 (1989). Creatine is phosphorylated chemically or enzymatically to creatine kinase to generate creatine phosphate, which is also well known (see, *The Merck Index*, No. 7315). Both creatine and creatine phosphate (phosphocreatine) can be extracted from animals or tissue or synthesized chemically. Both are commercially available.

Cyclocreatine is an essentially planar cyclic analogue of creatine. Although cyclocreatine is structurally similar to creatine, the two compounds are distinguishable both kinetically and thermodynamically. Cyclocreatine is phosphorylated efficiently by the enzyme creatine kinase in the forward reaction, both in vitro and in vivo. Rowley, G. L., *J. AM. Chem. Soc.*, 93:5542–5551 (1971); McLaughlin, A. C. et. al., *J. Biol. Chem.*, 247, 4382–4388 (1972). It represents a class of substrate analogues of creatine kinase and which are believed to be active.

Examples of creatine analogues known or believed to modify the creatine kinase/creatine phosphate system are listed in Tables 1 and 2.

TABLE 1

CREATINE ANALOGS

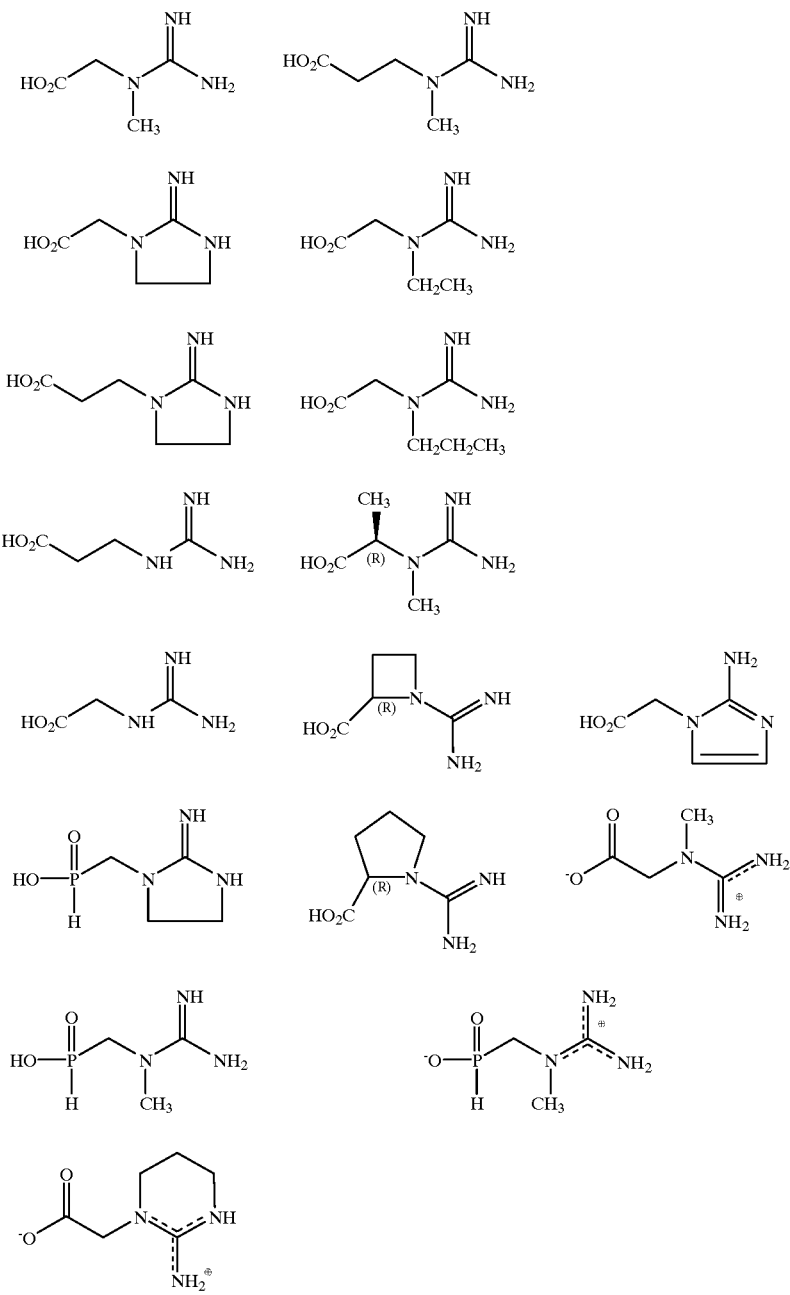

TABLE 2

CREATINE PHOSPHATE ANALOGS

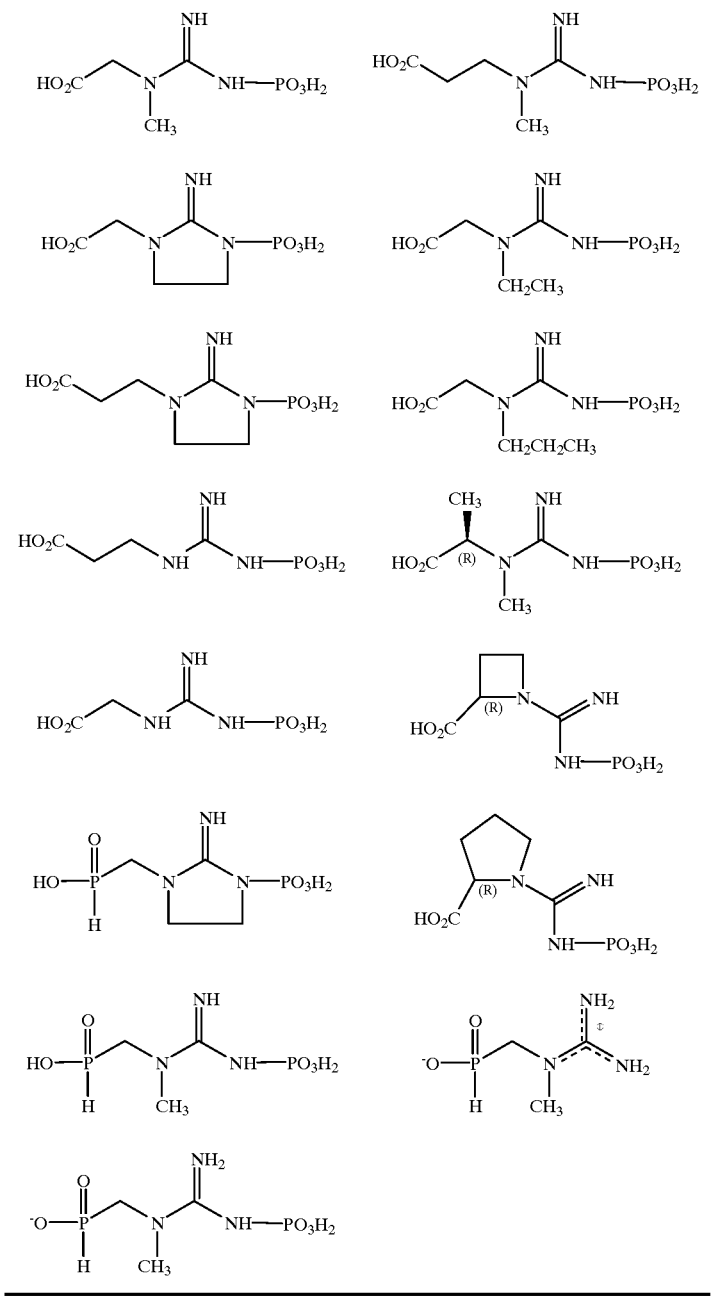

Most of these compounds have been previously synthesized for other purposes. Rowley et. al., *J. Am. Chem. Soc.,* 93:5542–5551 (1971); Mclaughlin et. al., *J. Biol. Chem.,* 247:4382–4388 (1972); Nguyen, A. C. K., "Synthesis and enzyme studies using creatine analogues", Thesis, Dept of Pharmaceutical Chemistry, Univ. Calif., San Francisco, (1983); Lowe et al., *J. Biol. Chem.,* 225:3944–3951 (1980); Roberts et. al., *J. Biol. Chem,* 260:13502–13508 (1995); Roberts et. al., *Arch. biochem. Biophy.,* 220:563–571 (1983), and Griffiths et. al., *J. Biol. Chem.,* 251:2049–2054 (1976). The contents of all of the aforementioned references are expressly incorporated herein by reference. Further to the aforementioned references, Kaddurah-Daouk et. al., (WO 92108456; WO 90/09192; U.S. Pat. Nos. 5,324,731; 5,321, 030) also provide citations for the synthesis of a plurality of creatine analogues. The contents of all the aforementioned references and patents are hereby incorporated herein by reference.

It is possible to modify the substances described below to produce analogues which have enhanced characteristics, such as greater specificity for the enzyme, enhanced solubility or stability, enhanced cellular uptake, or better binding activity. Salts of products may be exchanged to other salts using standard protocols.

Bisubstrate analogues of creatine kinase and non hydrolyizable substrate analogues of creatine phosphate (non transferable moieties which mimic the N phosphoryl group of creatine phosphate) can be designed readily and would be examples of creatine kinase modulators. Creatine phosphate compounds can be synthesized chemically or enzymatically. The chemical synthesis is well known. Annesley, T. M., Walker, J. B., *Biochem. Biophys. Res. Commun.*, 74:185–190 (1977); Cramer, F., Scheiffele, E., Vollmar, A., *Chem. Ber.*, 95:1670–1682 (1962).

Creatine compounds which are particularly useful in this invention include those encompassed by the following general formula:

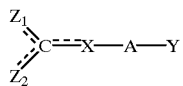

and pharmaceutically acceptable salts thereof, wherein:

a) Y is selected from the group consisting of: —CO$_2$H—NH)H, —NO$_2$, —SO$_3$H, —C(=O)NHSO$_2$J and —P(=O)(OH)(OJ), wherein J is selected from the group consisting of: hydrogen, C$_1$–C$_6$ straight chain alkyl, C$_3$–C$_6$ branched alkyl, C$_2$–C$_6$ alkenyl, C$_3$–C$_6$ branched alkenyl, and aryl;

b) A is selected from the group consisting of: C, CH, C$_1$–C$_5$alkyl, C$_2$–C$_5$alkenyl, C$_2$–C$_5$alkynyl, and C$_1$–C$_5$alkoyl chain, each having 0–2 substituents which are selected independently from the group consisting of:
  1) K, where K is selected from the group consisting of: C$_1$–C$_6$ straight alkyl, C$_2$–C$_6$ straight alkenyl, C$_1$–C$_6$ straight alkoyl, C$_3$–C$_6$ branched alkyl, C$_3$–C$_6$ branched alkenyl, and C$_4$–C$_6$ branched alkoyl, K having 0–2 substituents independently selected from the group consisting of: rromo, chloro, epoxy and acetoxy;
  2) an aryl group selected from the group consisting of: a 1–2 ring carbocycle and a 1–2 ring heterocycle, wherein the aryl group contains 0–2 substituents independently selected from the group consisting of: —CH$_2$L and —COCH$_2$L where L is independently selected from the group consisting of: bromo, chloro, epoxy and acetoxy; and
  3) —NH—M, wherein M is selected from the group consisting of: hydrogen, C$_1$–C$_4$ alkyl, C$_2$–C$_4$ alkenyl, C$_1$–C$_4$ alkoyl, C$_3$–C$_4$ branched alkyl, C$_3$–C$_4$ branched alkenyl, and C$_4$ branched alkoyl;

c) X is selected from the group consisting of NR$_1$, CHR$_1$, CR$_1$, O and S, wherein R$_1$ is selected from the group consisting of:
  1) hydrogen;
  2) K where K is selected from the group consisting of: C$_1$–C$_6$ straight alkyl, C$_2$–C$_6$ straight alkenyl, C$_1$–C$_6$ straight alkoyl, C$_3$–C$_6$ branched alkyl, C$_3$–C$_6$ branched alkenyl, and C$_4$–C$_6$ branched alkoyl, K having 0–2 substituents independently selected from the group consisting of: bromo, chloro, epoxy and acetoxy;
  3) an aryl group selected from the group consisting of a 1–2 ring carbocycle and a 1–2 ring heterocycle, wherein the aryl group contains 0–2 substituents independently selected from the group consisting of: —CH$_2$L and —COCH$_2$L where L is independently selected from the group consisting of: bromo, chloro, epoxy and acetoxy;
  4) a C$_5$–C$_9$ a-amino-w-methyl-w-adenosylcarboxylic acid attached via the w-methyl carbon;
  5) 2 C$_5$–C$_9$ a-amino-w-aza-w-methyl-w-adenosylcarboxylic acid attached via the w-methyl carbon; and
  6) a C$_5$–C$_9$ a-amino-w-thia-w-methyl-w-adenosylcarboxylic acid attached via the w-methyl carbon;

d) Z$_1$ and Z$_2$ are chosen independently from the group consisting of: =O, —NHR$_2$, —CH$_2$R$_2$, —NR$_2$OH; wherein Z$_1$ and Z$_2$ may not both be =O and wherein R$_2$ is selected from the group consisting of:
  1) hydrogen;
  2) K, where K is selected from the group consisting of: C$_1$–C$_6$ straight alkyl; C$_2$–C$_6$ straight alkenyl, C$_1$–C$_6$ straight alkoyl, C$_3$–C$_6$ branched alkyl, C$_3$–C$_6$ branched alkenyl, and C$_4$–C$_6$ branched alkoyl, K having 0–2 substituents independently selected from the group consisting of: bromo, chloro, epoxy and acetoxy;
  3) an aryl group selected from the group consisting of a 1–2 ring carbocycle and a 1–2 ring heterocycle, wherein the aryl group contains 0–2 substituents independently selected from the group consisting of: —CH$_2$L and —COCH$_2$L where L is independently selected from the group consisting of: bromo, chloro, epoxy and acetoxy;
  4) 2 C$_4$–C$_8$ a-amino-carboxylic acid attached via the w-carbon;
  5) B, wherein B is selected from the group consisting of: —CO$_2$H—NHOH, —SO$_3$H, —NO$_2$, OP(=O)(OH)(OJ) and —P(=O)(OH)(OJ), wherein J is selected from the group consisting of: hydrogen, C$_1$–C$_6$ straight alkyl, C$_3$–C$_6$ branched alkyl, C$_2$–C$_6$ alkenyl, C$_3$–C$_6$ branched alkenyl, and aryl, wherein B is optionally connected to the nitrogen via a linker selected from the group consisting of: C$_1$–C$_2$ alkyl, C$_2$ alkenyl, and C$_1$–C$_2$ alkoyl;
  6) —D—E, wherein D is selected from the group consisting of: C$_1$–C$_3$ straight alkyl, C$_3$ branched alkyl, C$_2$–C$_3$ straight alkenyl, C$_3$ branched alkenyl, C$_1$–C$_3$ straight alkoyl, aryl and aroyl; and E is selected from the group consisting of: —(PO$_3$)$_n$NMP, where n is 0–2 and NMP is ribonucleotide monophosphate connected via the 5'-phosphate, 3'-phosphate or the aromatic ring of the base; —[P(=O)(OCH$_3$)(O)]$_m$—Q, where m is 0–3 and Q is a ribonucleoside connected via the ribose or the aromatic ring of the base; —[P(=O)(OH)(CH$_2$)]$_m$—Q, where m is 0–3 and Q is a ribonucleoside connected via the ribose or the aromatic ring of the base; and an aryl group containing 0–3 substituents chosen independently from the group consisting of: Cl, Br, epoxy, acetoxy, —OG, —C(=O)G, and —CO$_2$G, where G is independently selected from the group consisting of: C$_1$–C$_6$ straight alkyl, C$_2$–C$_6$ straight alkenyl, C$_1$–C$_6$ straight alkoyl, C$_3$–C$_6$ branched alkyl, C$_3$–C$_6$ branched alkenyl, C$_4$–C$_6$ branched alkoyl, wherein E may be attached to any point to D, and if D is alkyl or alkenyl, D may be connected at either or both ends by an amide linkage; and
  7) —E, wherein E is selected from the group consisting of —(PO$_3$)$_n$NMP, where n is 0–2 and NMP is a ribonucleotide monophosphate connected via the 5'-phosphate, 3'-phosphate or the aromatic ring of the base; —[P(=O)(OCH$_3$)(O)]$_m$—Q, where m is 0–3 and Q is a ribonucleoside connected via the ribose or the aromatic ring of the base; —[P(=O)(OH)(CH$_2$)]$_m$—Q, where m is 0–3 and Q is a ribonucleoside connected via the ribose or the aromatic ring of the base; and an aryl group containing 0–3 substituents chose independently from the group consisting of: Cl, Br, epoxy, acetoxy, —OG, —C(=O)G, and —CO$_2$G, where G is independently selected from the group consisting of: C$_1$–C$_6$ straight alkyl, C$_2$–C$_6$ straight alkenyl, C$_1$–C$_6$ straight alkoyl, C$_3$–C$_6$ branched alkyl, C$_3$–C$_6$ branched alkenyl, C$_4$–C$_6$ branched alkoyl; and if E is aryl, E may be connected by an amide linkage;

e) if R$_1$ and at least one R$_2$ group are present, R$_1$ may be connected by a single or double bond to an R$_2$ group to form a cycle of 5 to 7 members;

f) if two R$_2$ groups are present, they may be connected by a single or a double bond to form a cycle of 4 to 7 members; and g) if R$_1$ is present and Z$_1$ or Z$_2$ is selected from the group consisting of —NHR$_2$, —CH$_2$R$_2$ and —NR$_2$OH, then R$_1$ may be connected by a single or double bond to the carbon or nitrogen of either Z$_1$ or Z$_2$ to form a cycle of 4 to 7 members. Currently preferred compounds include cyclocreatine, creatine phosphate and those included in Tables 1 and 2 hereinabove.

The modes of administration for these compounds include, but are not limited to, oral, transdermal, or parenteral (e.g., subcutaneous, intramuscular, intravenous, bolus or continuous infusion). The actual amount of drug needed will depend on factors such as the size, age and severity of disease in the afflicted individual. Creatine has been administered to athletes in the range of 2–8 gms/day to improve muscle function. Creatine phosphate was administered to patients with congestive heart failure also in the range of several gm/day, and was very well tolerated. In experimental animal models of cancer or viral infections, where creatine compounds have been shown to be active, amounts of 1 gm/kg/day were administered intravenously or intraperitoneially. For this invention the creatine compound will be administered at dosages and for periods of time effective to reduce, ameliorate or eliminate the symptoms of the disease. Dose regimens may be adjusted for purposes of improving the therapeutic or prophylactic response of the compound. For example, several divided doses may be administered daily, one dose, or cyclic administration of the compounds to achieve the desired therapeutic result. Agents that improve the solubility of these compounds could also be added.

The creatine compounds can be formulated with one or more adjuvants and/or pharmaceutically acceptable carriers according to the selected route of administration. The addition of gelatin, flavoring agents, or coating material can be used for oral applications. For solutions or emulsions in general, carriers may include aqueous or alcoholic/ aqueous solutions, emulsions or suspensions, including saline and buffered media. Parenteral vehicles can include sodium chloride, potassium chloride among others. In addition, intravenous vehicles can include fluid and nutrient replenishers, electrolyte replenishers among others.

Preservatives and other additives can also be present. For example, antimicrobial, antioxidant, chelating agents, and inert gases can be added (see, generally, Remington's Pharmaceutical Sciences, 16th Edition, Mack, (1980)).

The present invention is demonstrated more fully by the following examples, which are not intended to be limiting in any way:

EXAMPLE 1

Effect of Creatine Compounds on Glucose Levels in Rats Bearing Tumors

Two creatine compounds, creatine phosphate and cyclocreatine, were injected intravenously into tumor bearing rats, and the level of glucose in the rats was monitored. Beta guanidino propionic acid, also was administered. This compound was previously shown to have no effect on glucose levels in normal animals but was shown to modify glucose levels in NIDDM models. There was no specific reason for using tumor bearing rats, except convenience because the antitumor activity of these compounds also was being studied. The presence of the tumors should not have any effect on the ability of these compounds to regulate glucose levels.

The rats carrying the tumors were described by us previously (see, Teisher et al., *Cancer Chemother. Pharmacol*, 35:411–416, 1995). The schedule and dose selected in these experiments was based on prior experience working with this class of compounds as anticancer or antiviral chemotherapeutic agents. The rat mammary adenocarcinoma 13762 was implanted in the female Fisher 344 rats on day zero. The creatine compounds were administered intravenously on days 4–8 and days 14–18. The amounts used were 1 gm/kg of cyclocreatine, 0.93 gm/kg for beta guanidino propionic acid, and 2.32 gm/kg for creatine phosphate. We were targeting a 1 gm/kg molar equivalent of creatine to achieve mM levels known typically to be needed with creatine analogues to modulate the creatine kinase system intracellularly. Plasma glucose levels were measured at around 11 a.m., by taking a drop of blood from the animals and testing glucose levels using a commercial kit (CHEMSTRIP bG, Boehringer Mannheim). For animals that were treated with drugs, the treatment was around 9 a.m., and bleeding was also at around 11 a.m.

FIG. 1 shows the results of our first experiment graphically. Panel (A): glucose levels in control (unmanipulated animals); Panel (B): glucose levels in cyclocreatine treated animals; Panel (C): glucose levels in beta-guanidino propionic acid treated animals; and Panel (D): glucose levels in creatine phosphate treated animals. The controls showed an average glucose level in rats of 62 mg/dl. The treatment with cyclocreatine showed two drops in glucose levels at the time of drug administration, i.e., between days 4–8 and days 14–18. The drop in glucose level at the second cycle of drug administration was more dramatic than the first cycle, consistent with what is known about the continuous build up of these compounds in organs high in creatine kinase activity. Minimal changes in glucose levels were seen with beta guanidino propionic acid treatment consistent with previous published data. The compound creatine phosphate induced similar pattern of drops in glucose levels as that seen with cyclocreatine, although cyclocreatine seemed to be more potent.

EXAMPLE 2

Effect of Creatine Compounds on Glucose Levels in Rats Bearing Tumors

The same experiment described above was repeated. FIG. 2 shows the effect of the selected compounds on glucose levels. Panel (A): control (unmanipulated animals); Panel (B): cyclocreatine treated; Panel (C): beta-guanidino propionic acid treated; Panel (D): creatine phosphate treated animals. The same pattern seen in Example 1 is also seen here. Cyclocreatine induced a drop in the level of glucose after each administration. The drop in the second cycle was more dramatic than the first. Beta-guanidino propionic acid had minimal effect, and creatine phosphate seemed to mirror the effect of cyclocreatine.

EXAMPLE 3

Effect of Creatine Compounds on Glucose Levels in Rats Bearing Tumors

Figure 3A:
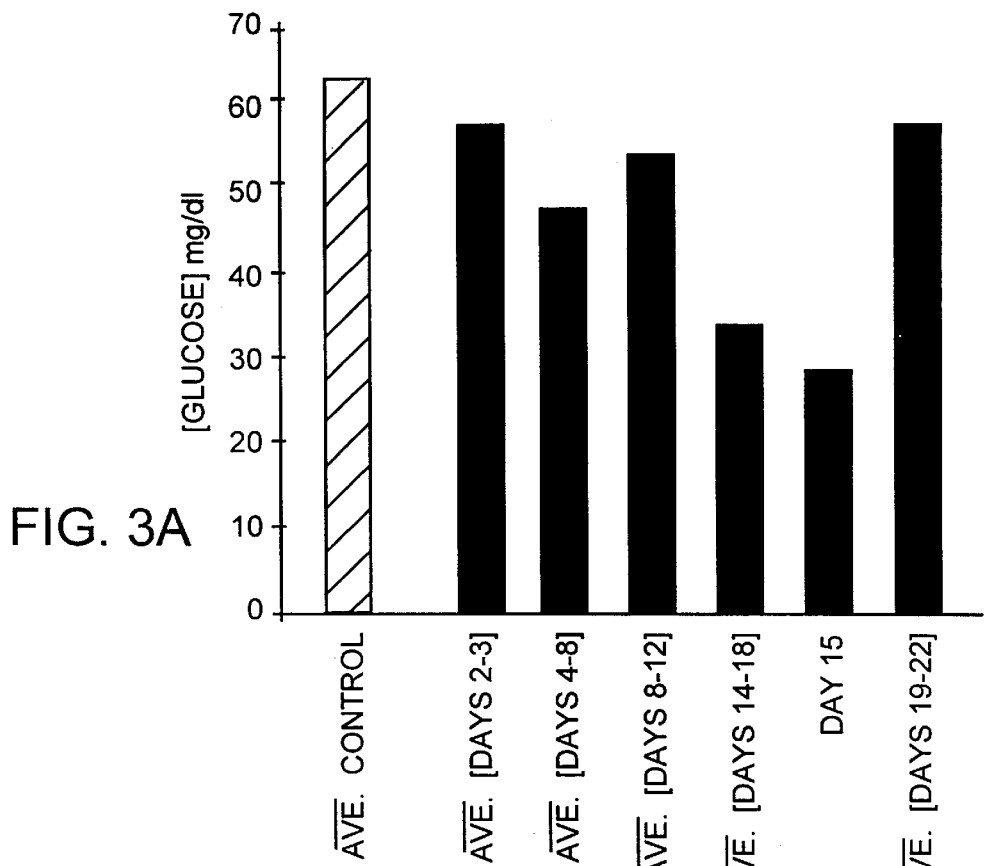
FIG. 3 graphically illustrates the average effect of selected creatine compounds on glucose levels in rats over time: Panel (A): illustrates average glucose levels in cyclocreatine treated animals as compared to the average of the control (unmanipulated animals); Panel (B): illustrates average glucose levels in beta-guanidino propionic acid treated animals as compared to the average of the control (unmanipulated animals); Panel (C): illustrates average glucose levels in creatine phosphate treated animals as compared to the average of the control (unmanipulated animals).
Figure 3B:
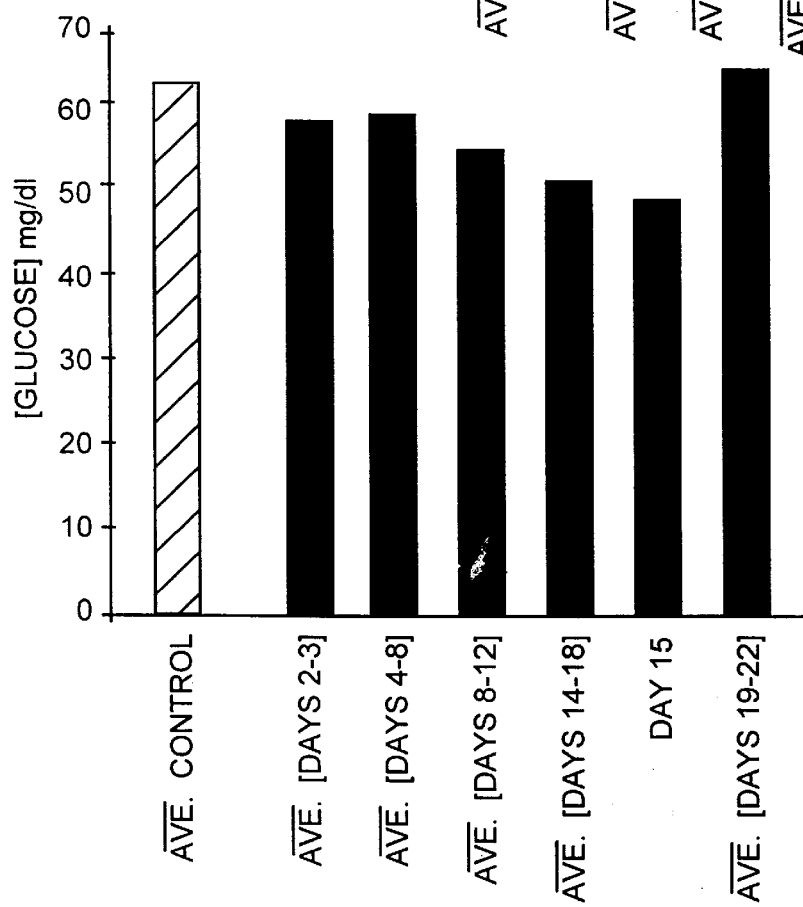
Figure 3C:
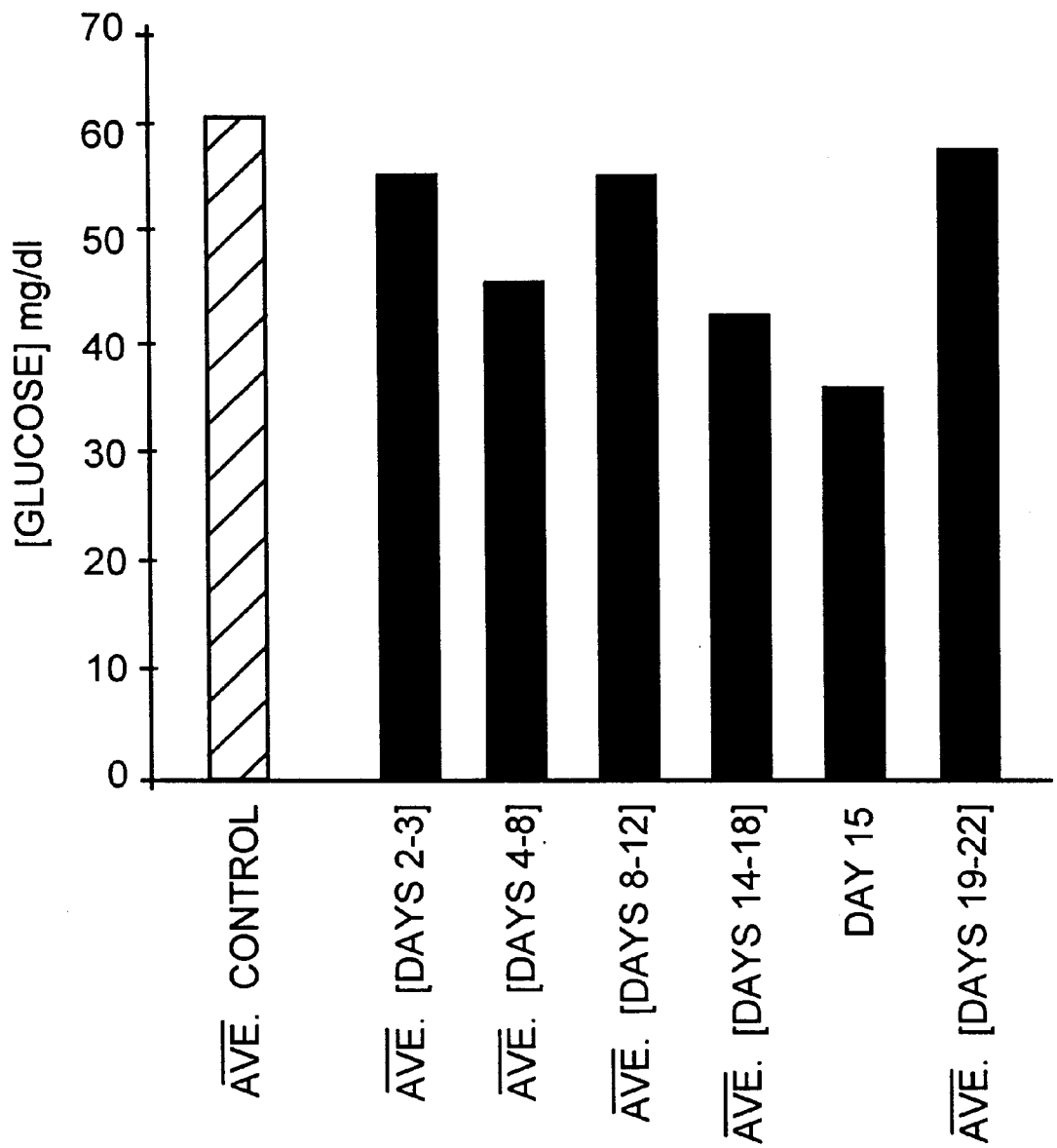

To examine more closely what occurred in the above two experiments, the average readings of glucose levels from experiments one and two were taken in the following time intervals post drug treatment: Days 2–3, Days 4–8, Days 8–12, Days 14–18, Day 15 and Days 19–22. Day 15 demonstrates the largest effect on glucose levels by this class of compounds. FIG. 3 outlines these results. Cyclocreatine, Panel (A), shows a drop in glucose level that could be as high as 50% on day 15. Beta-guanidino propionic acid, Panel (B), shows minimal effects <15%, and creatine phosphate, Panel (C), seems to drop glucose levels by 35% on day 15.

The experiments described above demonstrate that creatine analogues which modulate the creatine kinase system, and that are represented by cyclocreatine and creatine phosphate, can regulate glucose levels. The creatine kinase enzyme system creatine kinase emerges as a novel target for drug design for diseases related to the control of glucose levels.

EXAMPLE 4

Effect of Cyclocreatine on Glucose Levels in Rabbits

The creatine compound cyclocreatine, was given as a continuous intravenous infusion (IV) to normal rabbits or rabbits infected with the human cytomegalovirus (HCMV) in their eyes (Rabbit Chorioretinal model). Glucose levels were recorded over a period of seven days. This compound was tested in infected as well as in normal animals due to the fact that these compounds were also being evaluated as anti viral agents, a biological activity that were reported in the U.S. Pat. No. 5,321,030. As will become clear in the data presented here the eye infection had no effect on the levels of glucose recorded. The schedule and dose selected in these experiments was based on prior experience working with this class of compounds as antiviral agents.

A total of 11 NZW rabbits weighing 1.75–2.0 Kg were used in the experiments. All animals were infused with various doses of cyclocreatine over a period of 1–7 days in a continuous infusion mode. Continuous infusions were achieved by surgical implantation of an indwelling catheter implant into the jugular vein by standard surgical procedures. The catheter was threaded through a steel sleeve and swivel apparatus attached to the back of the animal's neck which was anchored to a specially fitted vest. A Harvard Apparatus 2200 unifusion pump maintained drug delivery at a constant rate through out the experiment. This arrangement allowed the animal unimpaired movement within its cage. Animals received a bolus injection of antibiotics immediately after surgery and daily if needed. After animals recovered from the anesthesia, some animals were inoculated by intravitreal injection of AD169 HCMV ($10^5$ pfu). The remaining animals were left uninfected. Both infected and uninfected animals received a continuous infusion of cyclocreatine or saline for up to seven days. Concentrations of cyclocreatine were 5, 10, or 15 mg cyclocreatine/mil saline and infusion rates and volumes were adjusted to achieve the desired dose of 375–1125 mg/Kg/day. These concentrations were based on amounts required to achieve other biological activities such as antiviral or anticancer. Volumes did not exceed the animal's normal daily intake of fluids (based upon the assumed water consumption of roughly 100–150 ml/Kg/day; Harknes and Wagner, 1985). The rest of the animals received a similar volume of sterile saline. On days 0, 1, 3, 5 and 7 blood was withdrawn from the ear veins and glucose levels were determined.

Blood glucose levels in these rabbits that were allowed to freely feed ranged from 169–201 mg/dl. The average level determined in this assay was around 177 mg/dl which is slightly higher than that reported for rabbits in the fasting state. Table 3 summarizes levels of glucose in treated and untreated animals over a period of up to seven days.

TABLE 3

Glucose Levels In Cyclocreatine Infused Rabbits

| Drug Conc. (mg/ml) | 0 | 5 | 5 | 5 | ave 5 | 10 | 10 | 10 | 10 | ave 10 | 15 | 15 | 15 | ave 15 |
|---|---|---|---|---|---|---|---|---|---|---|---|---|---|---|
| Infected (HCMV) | yes | yes | yes | yes | | yes | yes | yes | yes | | no | no | no | |
| 0 | 177 | 177 | 177 | 177 | 177 | 169 | 194 | 201 | 184 | 187 | 177 | 177 | 177 | 177 |
| 1 | 152 | 104 | 94 | 93 | 97 | 118 | 89 | 76 | 81 | 91 | | | | |
| 3 | 179 | 70 | 49 | 47 | 55 | 103 | 98 | 74 | 85 | 90 | 48 | 59 | | 54 |
| 4 | | | | | | 59 | 69 | 87 | 65 | 70 | | | | |
| 5 | | 29 | 41 | 33 | 34 | 45 | 62 | 55 | 53 | 54 | | 7 | 22 | 15 |
| 6 | | | | | | | | | | | | | 22 | 22 |
| (10 ml/rabbit 20% Dextrose)* 7 | | | | | | | | | | | | | 73 | 73 |

Figure 4A:
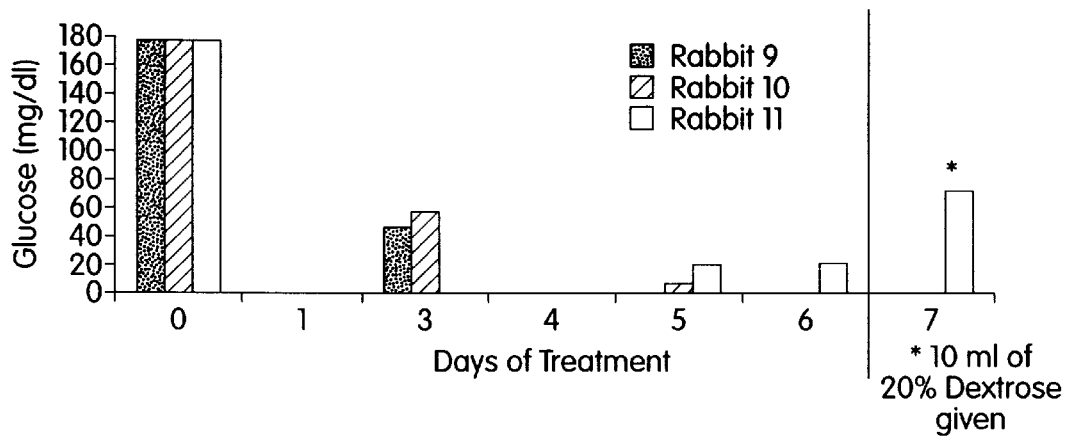
FIG. 4 graphically illustrates the effect of cyclocreatine on glucose levels in rabbits infused with cyclocreatine. Rabbits or HCMV infected rabbits were infused in a continuous intravenious mode with cyclocreatine as outlined in Example 4. The cyclocreatine solution was prepared in saline at 5 mg/ml, 10 mg/ml or 15 mg/ml and was infused to deliver amounts of drug 375–1125 mg/Kg/day. Cyclocreatine was infused daily for up to 7 days. Glucose levels were determined using standard procedures (BioPure, Boston, Mass.) on several days and up to the end of the cyclocreatine infusion. Glucose levels were determined on several days and up to 7 days post cyclocreatine infusion. Panel (A) illustrates the effect of cyclocreatine infused at 15 mg/ml on blood glucose levels of normal rabbits. Each bar represents glucose levels in separate animals. Panel (B) illustrates the effect of cyclocreatine infused at 10 mg/ml on blood glucose levels in infected rabbits. Each bar represents glucose levels in separate animals. Panel (C) illustrates the effect of cyclocreatine infused at 5 mg/ml on blood glucose levels of infected rabbits. Each line represents glucose levels in separate animals.
Figure 4B:
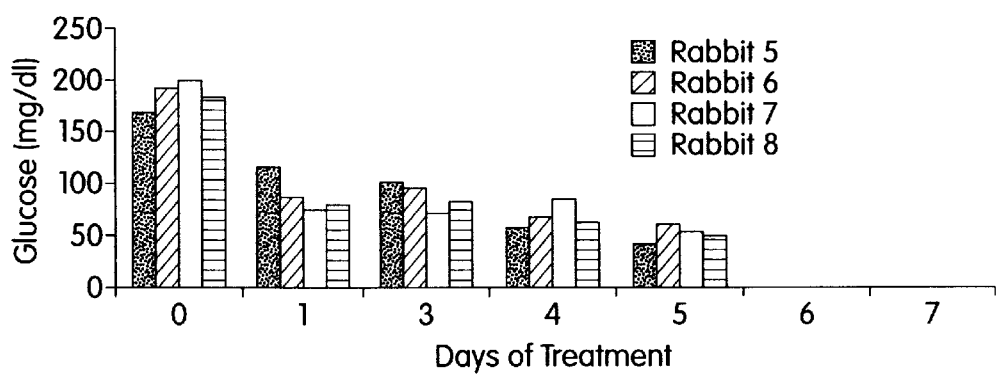
Figure 4C:
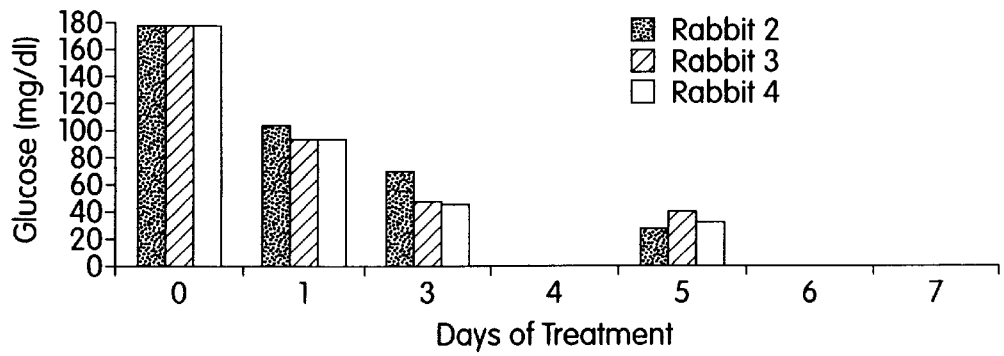
Figure 5:
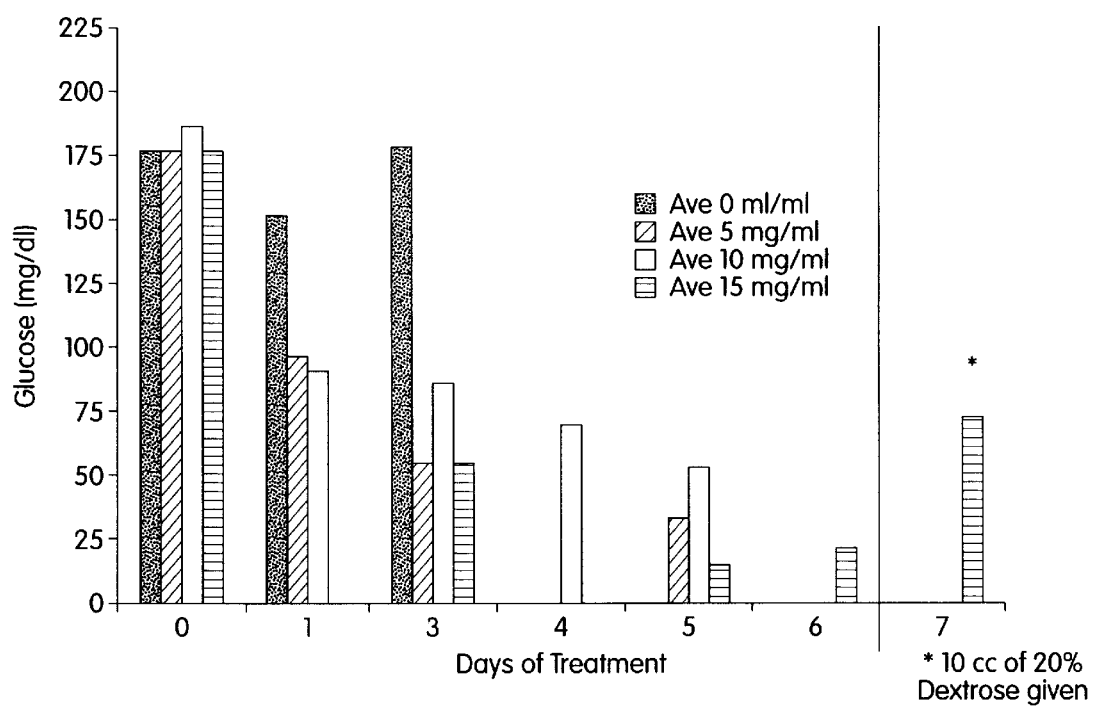
FIG. 5 graphically illustrates the average effect of infused cyclocreatine on glucose levels in rabbits. Animals infused with saline or cyclocreatine at different concentrations were examined for glucose levels for up to seven days post infusion. At each concentration of cyclocreatine glucose levels were determined in 3–4 animals and average values were calculated and presented as bars.

FIG. 4 illustrates graphically the effect of cyclocreatine glucose levels on each treated animal, and FIG. 5 illustrates the average effects on glucose levels seen in these animals. As shown in Table 3 and FIGS. (4 and 5), animals that were uninfected and treated with cyclocreatine at a dose of 15 mg/ml (1125 mg/Kg/day) experienced a significant drop in their glucose levels. By day three glucose levels were in the range of 48–59 mg/dl; by day five they were 7–22 mg/dl and the animals became very lethargic. The administration of 10 mls of a 20% solution of dextrose on day 7 brought back the level of glucose to 70 mg/dl and the animals seemed to quickly recover and resumed normal activity and eating. These data clearly suggest that cyclocreatine is a potent regulator of blood glucose levels and that the creatine kinase system must be involved in glucose metabolism and homeostasis. Lower doses of cyclocreatine were tested in infected animals. At doses of 10 mg/ml (750 mg/Kg/day) and 5 mg/ml (375 mg/Kg/day) the same observation was noted, ie a significant drop in blood glucose levels (Table 3 and FIGS. 4 and 5). As early as day one drops in glucose levels were noted with averages going down to the 90mg/dl range and by day five the range was in the 30–50 mg/dl. Some glucose levels in the animals treated with 5 mg/ml cyclocreatine seem to have a lower level than those treated with 10 mg/ml.

We believe this is experimental variation due to the complexity of the setting requiring experiments to be done on separate days. What is very clear from all of these experiments is that cyclocreatine has definite and very reproducible effects on lowering blood glucose levels in rabbits. Infections in the eye do not seem to have an impact on blood glucose levels, as animals infected and infused with saline experienced no drop in blood glucose Table 3. These saline infused animals also illustrate that saline alone has no effect on blood glucose levels.

EXAMPLE 5

The Effect of Cyclocreatine on Glucose Levels and Insulin in a Diabetic Animal This preliminary study was initiated to gain insight into the potential regulation of glucose levels by creatine compounds in ZDF rats, a widely studied rodent model of NIDDM (Peterson, Lessons from *Animal Diabetes*, 1994, Pages 225–230). Male Zuker diabetic fatty (ZDF-fa/fa) rats and their lean Zuker littermates (ZDF +/?) were from Genetic Models, Inc., Indianapolis, Ind. This model shows diabetic characteristics which appear to mimic human adult onset diabetes. Hyperglycemia is initially manifested at about 7 weeks of age and all obese rats are fully diabetic by 12 weeks of age (fed blood glucose of greater than 500 mg %). This level of hyperglycemia increases slightly for several weeks thereafter. Between 7 and 10 weeks, blood insulin levels are high but these subsequently drop as the pancreatic beta cells cease to respond to the glucose stimulus. The lean (ZDF/Gmi) rats are the control counterparts of the diabetic animals. These rats have the same genetics as the obese animals except for the obesity trait. No phenotypic differences have been observed between these rats and other typical lean control rats. Hence these animals represent an excellent control for the obese diabetic animals.

Figure 6:
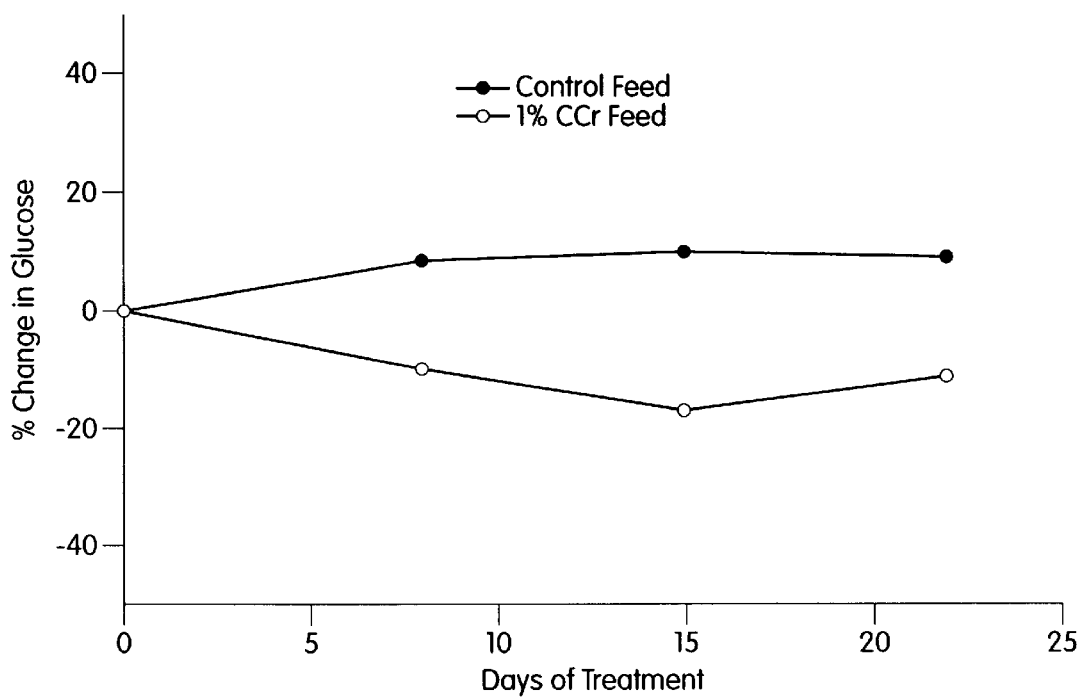
FIG. 6 graphically illustrate the average effect of cyclocreatine over time on glucose levels in the Male Zuker lean littermates (+/?) as compared to Day 0. Three animals per group were treated with the compound in the feed as described in Example 5. Solid circles (●) are averages in untreated groups while open circles (○) are averages in treated groups.
Figure 7:
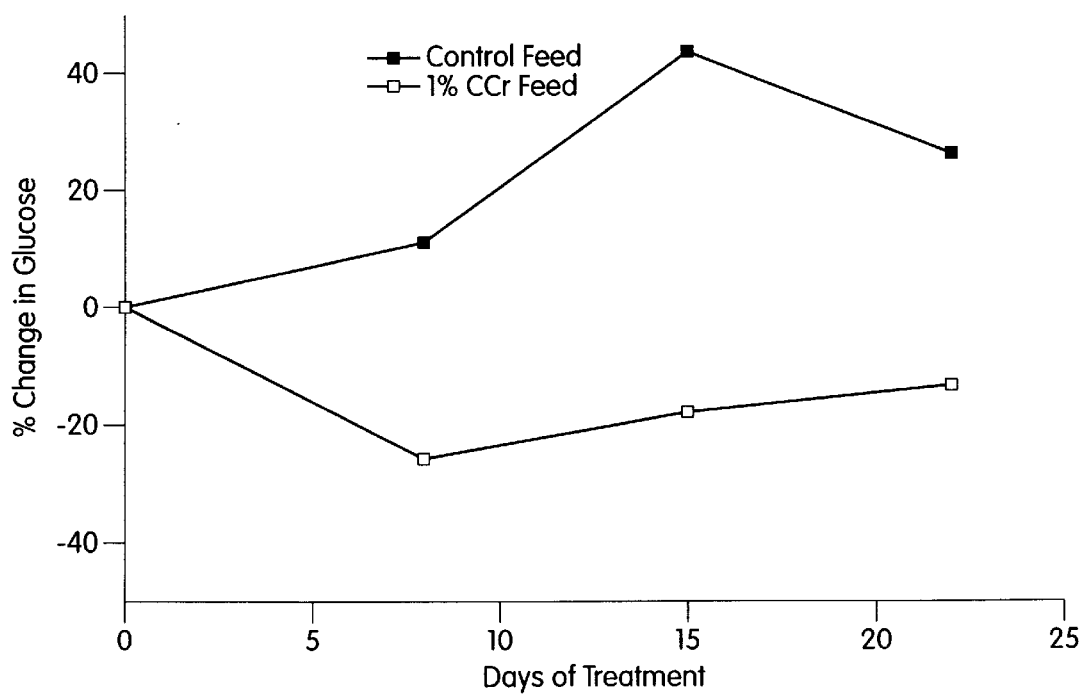
FIG. 7 graphically illustrates the average effect of cyclocreatine over time on glucose levels in the Male Zuker diabetic fatty (ZDF-fa/fa) rats as compared to Day 0. Three animals per group were treated with the compound in the feed as described in Example 5. Solid squares (■) are averages in untreated groups while open squares (□) are averages in treated groups.
Figure 8:
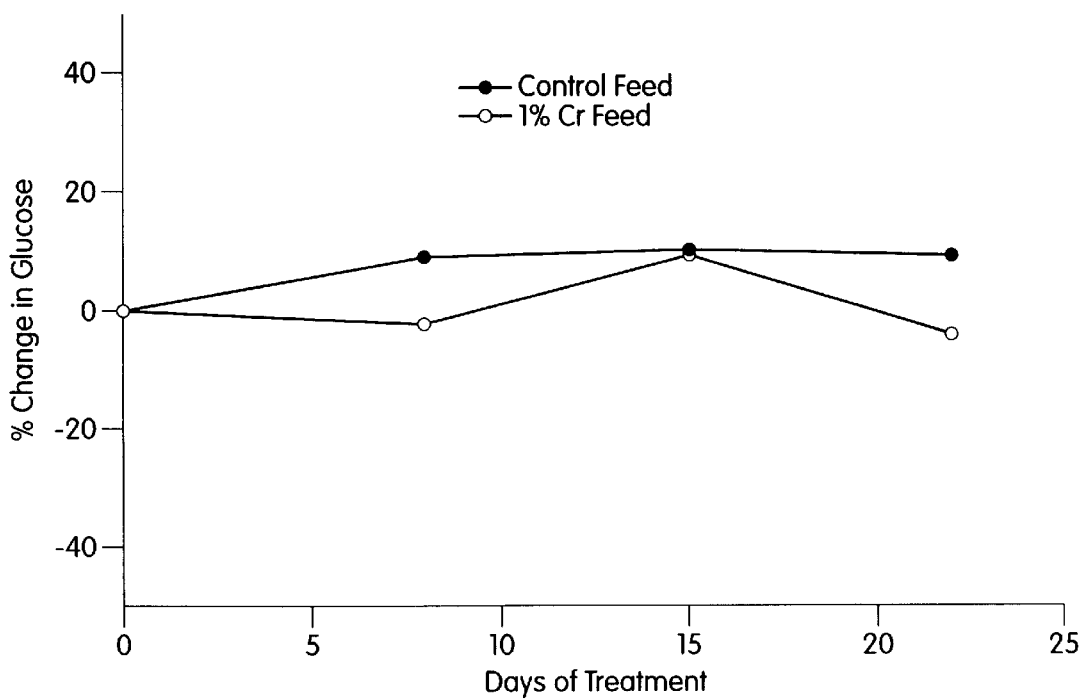
FIG. 8 graphically illustrate the average effect of creatine over time on glucose level in the Male Zuker lean littermates (+/?) as compared to Day 0. Three animals per group were treated with the compound in the feed as described in Example Five. Solid circles (●) are averages in untreated groups while open circles (○) are averages in treated groups.
Figure 9:
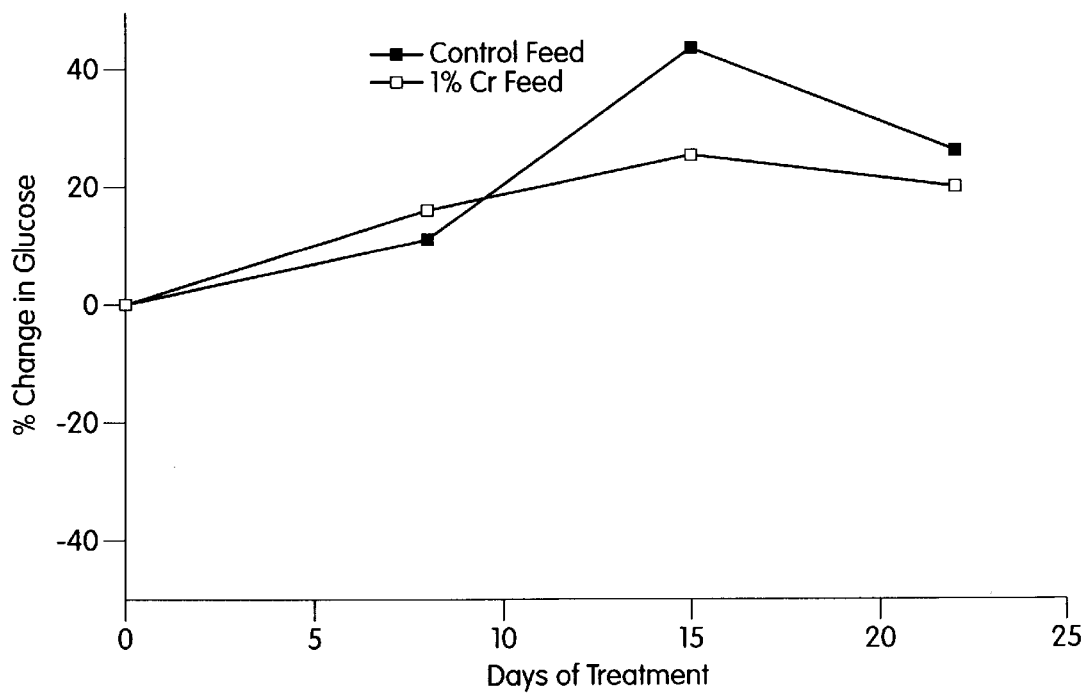
FIG. 9 graphically illustrates the average effect of creatine over time on glucose levels in the Male Zuker diabetic fatty (ZDF-fa/fa) rats as compared to Day 0. Three animals per group were treated with the compound in the feed as described in Example 5. Solid squares (■) are averages in untreated groups while open squares (□) are averages in treated groups.
Figure 10:
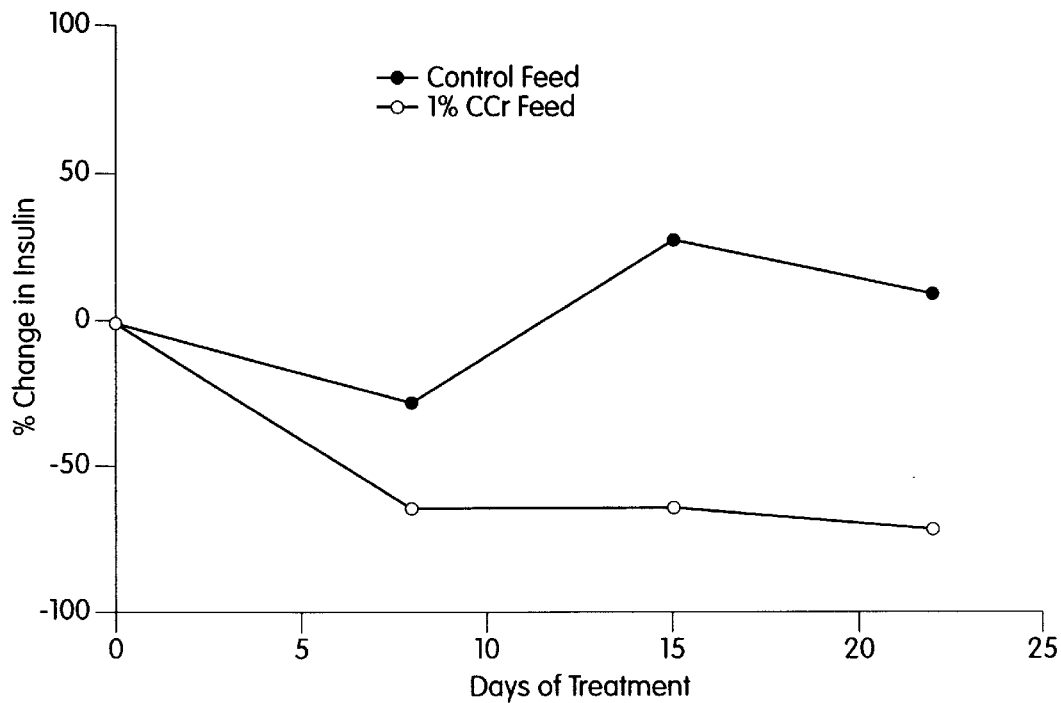
FIG. 10 graphically illustrate the average effect of cyclocreatine over time on insulin level in the Male Zuker lean littermates (+/?) as compared to Day 0 Three animals per group were treated with the compound in the feed as described in Example 5. Solid circles (●) are averages in untreated groups while open circles (○) are averages in treated groups.
Figure 11:
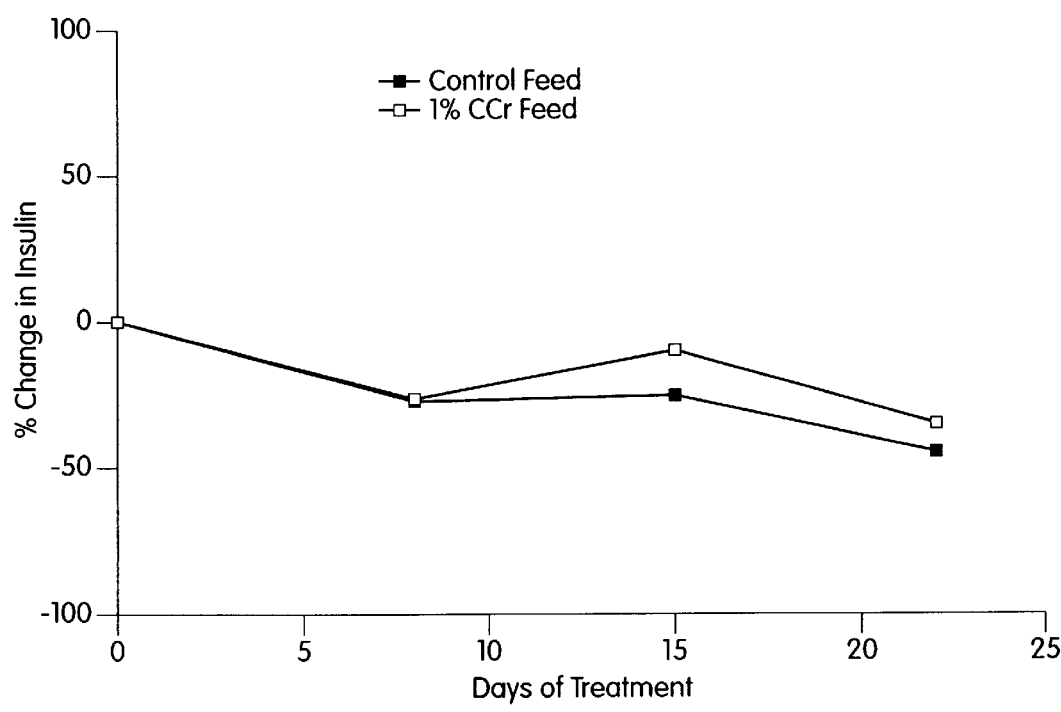
FIG. 11 graphically illustrates the average effect of cyclocreatine over time on insulin levels in the Male Zuker diabetic fatty (ZDF-fa/fa) rats as compared to Day 0. Three animals per group were treated with the compound in the feed as described in Example 5. Solid squares (■) are averages in untreated groups while open squares (□) are averages in treated groups.
Figure 12:
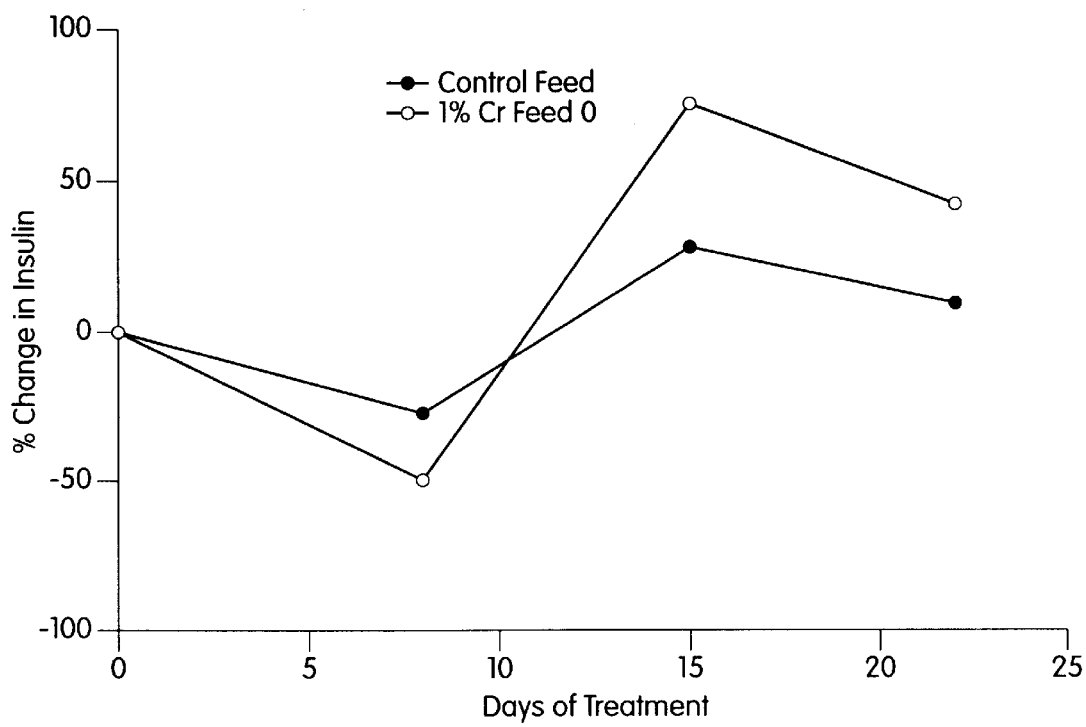
FIG. 12 graphically illustrate the average effect of creatine over time on insulin level in the Male Zuker lean littermates (+/?) as compared to Day 0. Three animals per group were treated with the compound in the feed as described in Example 5. Solid circles (●) are averages in untreated groups while open circles (○) are averages in treated groups.
Figure 13:
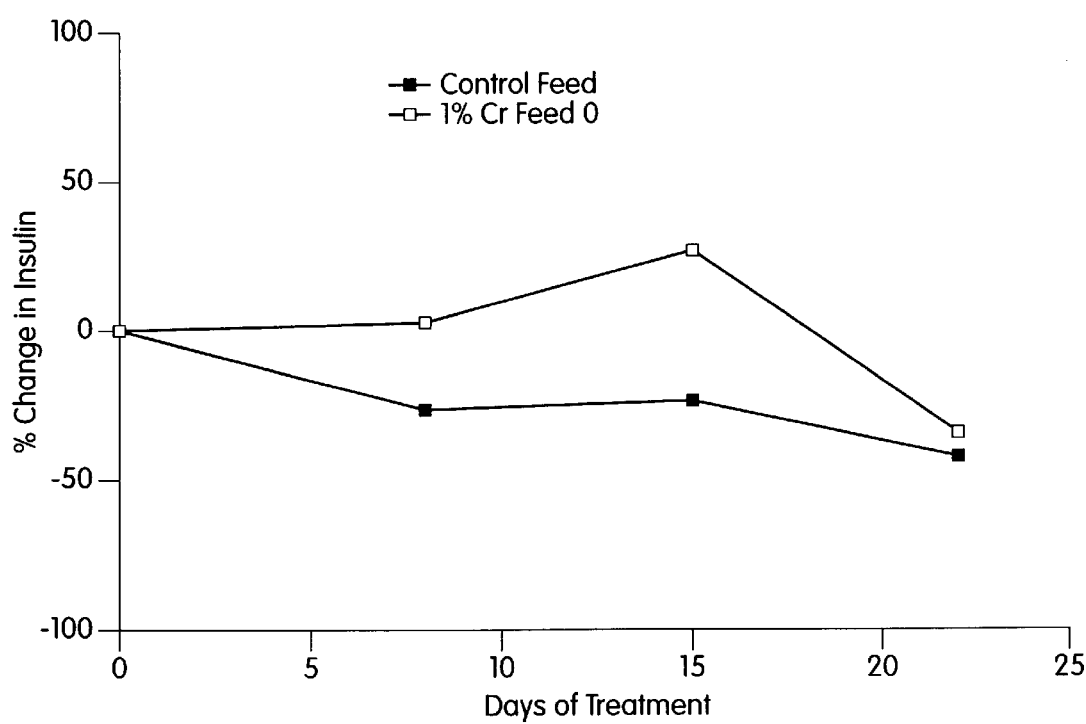
FIG. 13 graphically illustrates the average effect of creatine over time on insulin levels in the Male Zuker diabetic fatty (ZDF-fa/fa) rats as compared to Day 0. Three animals per group were treated with the compound in the feed as described in Example 5. Solid squares (■) are averages in untreated groups while open squares (□) are averages in treated groups.

Male Zuker diabetic fatty (ZDF-fa/fa) rats and Zuker lean littermates (ZDF +/?) were 12 weeks old when dosing with creatine compounds was initiated. The ZDF-fa/fa rats were completely diabetic. The littermates were the same age. The average weight and food intake was 360 gm and 28 gm/day for the ZDF fatty rats and 300 gm and 20 gm/day for their lean littermates. Animals were housed and dosed 3 per cage. Untreated animals were fed Purina modified lab chow 5001. The creatine compounds cyclocreatine and creatine were given in the feed as 1% of the diet. The Purina rodent chow (5001) was formulated to contain 1% creatine or 1% cyclocreatine. Formulations were prepared by Purina Test Diets, Richmond, Ind. Both treated and untreated animals feed ad libitum and had free access to water. Animals were bled regularly throughout the experiment and glucose and insulin levels were determined using standard procedures (Linco RI-13K). FIGS. 6 and 7 illustrate the average (n=3) effect of cyclocreatine over time on glucose levels in the lean and fatty diabetic animals respectively. FIGS. 8 and 9 illustrate the average (n=3) effect of creatine over time on glucose levels in the lean and fatty diabetic animals respectively. FIGS. 10 and 11 illustrate the average (n=3) effect of cyclocreatine over time on insulin levels in the lean and fatty diabetic animals respectively. FIGS. 12 and 13 illustrate the average (n=3) effect of creatine over time on insulin levels in the lean and fatty diabetic animals respectively. Cyclocreatine as 1% of the diet dropped the level of glucose in the lean rats by about 15% (FIG. 6). In the obese diabetic animals, glucose levels in the untreated groups continued to rise by up to 40% (FIG. 7) while those on cyclocreatine experienced a drop of close to 20%. This illustrates that cyclocreatine is capable of regulating glucose levels in the diabetic state. Creatine had minimal effect on glucose levels in both the lean and the diabetic animals (FIGS. 8, 9).

FIG. 10 illustrates the average effect of cyclocreatine on insulin levels in lean animals which seem to drop significantly over 50%. FIG. 11 illustrates the average effect on insulin levels in obese fatty animals which seem to be minimally affected. FIG. 12 illustrates the average effect of creatine on insulin levels in lean animals which seems to show a modest up regulation, and FIG. 13 illustrates the average effect of creatine on insulin levels in obese fatty animals which also seem to be slightly elevated.

EXAMPLE 6

The Effect of Cyclocreatine on Glucose Levels in Cancer Patients

Cyclocreatine was tested in humans in a phase I/II open label dose escalation study. The patient population was terminal cancer patients because cyclocreatine has demonstrated antitumor activity when used as a single agent or in combination therapy. Cyclocreatine was administered at doses that ranged from 10 mg/Kg to 100 mg/Kg. The schedule of administration of cyclocreatine is described in Table 4.

TABLE 4

Table II: Clinical Schedule of Cyclocreatine Dose Administration in Cancer Patients

| | WEEK | | | | | | | | | | | | | | | | | | | | | | | |
|---|---|---|---|---|---|---|---|---|---|---|---|---|---|---|---|---|---|---|---|---|---|---|---|---|
| DAY | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| DOSING | x | | | | | | | x | x | | | | | | x | x | x | | | | | x | x | x |
| | WEEK | | | | | | | | | | | | | | | | | | | | | | | | |
| DAY | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 |
| DOSING | x | | | x | x | x | x | x | | | | | | | | | | | | | | | | |
| | WEEK | | | | | | | | | | | | | | | | | | | | | | | | |
| DAY | 49 | 50 | 51 | 52 | 53 | 54 | 55 | 56 | 57 | 58 | 59 | 60 | 61 | 62 | 63 | 64 | 65 | 66 | 67 | 68 | 69 | 70 |  |  |
| DOSING | | x | x | x | x | x | | | | | | | | | | | | | | | | | | |

Figure 14:
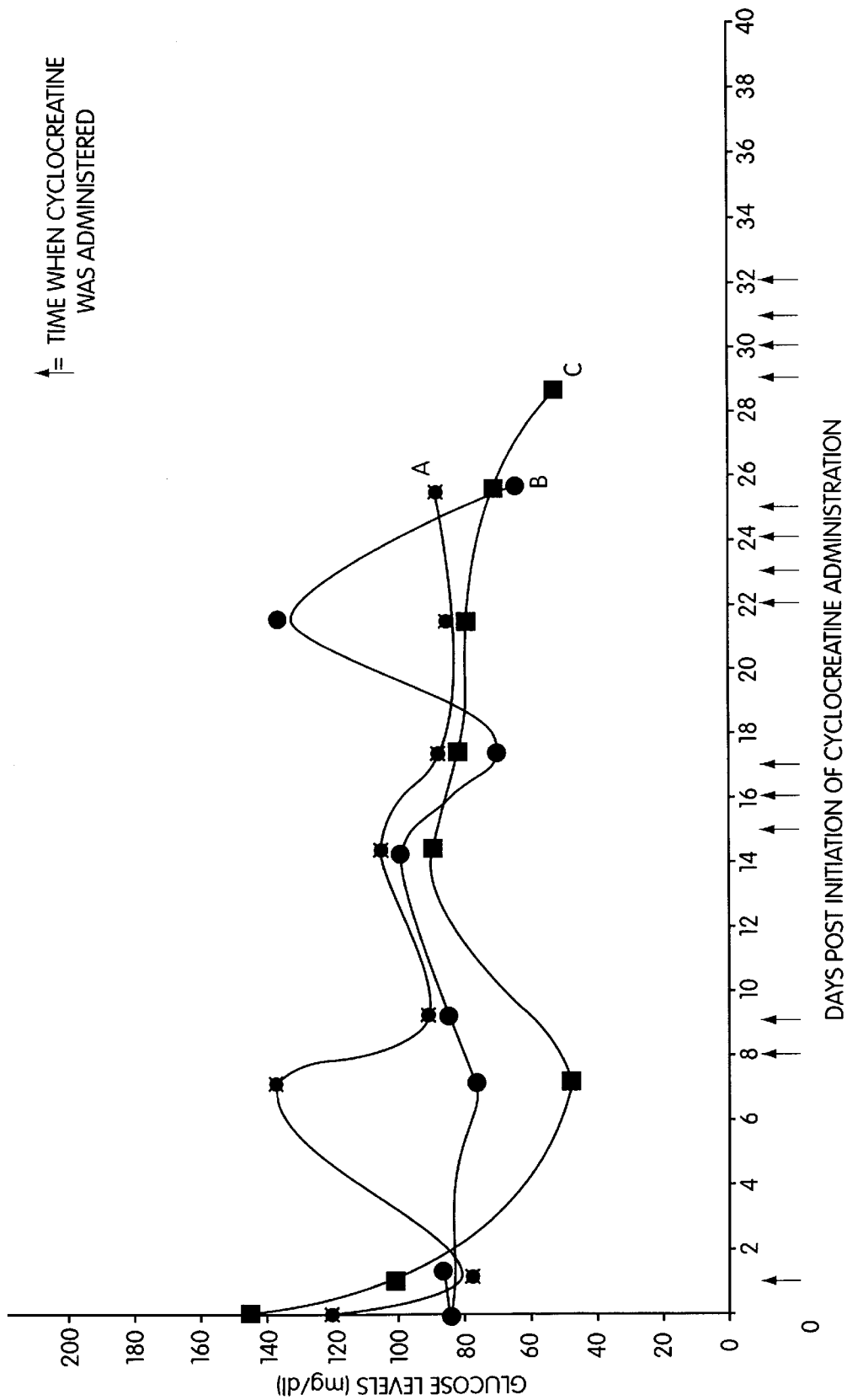
FIG. 14 graphically illustrates three individual patients' glucose levels upon treatment with cyclocreatine at a dose of 60 mg/Kg. Patients were treated with cyclocreatine via a 3 hour continuous infusion in a one liter volume of saline using the schedule of administration as described in Example 6.
Figure 15:
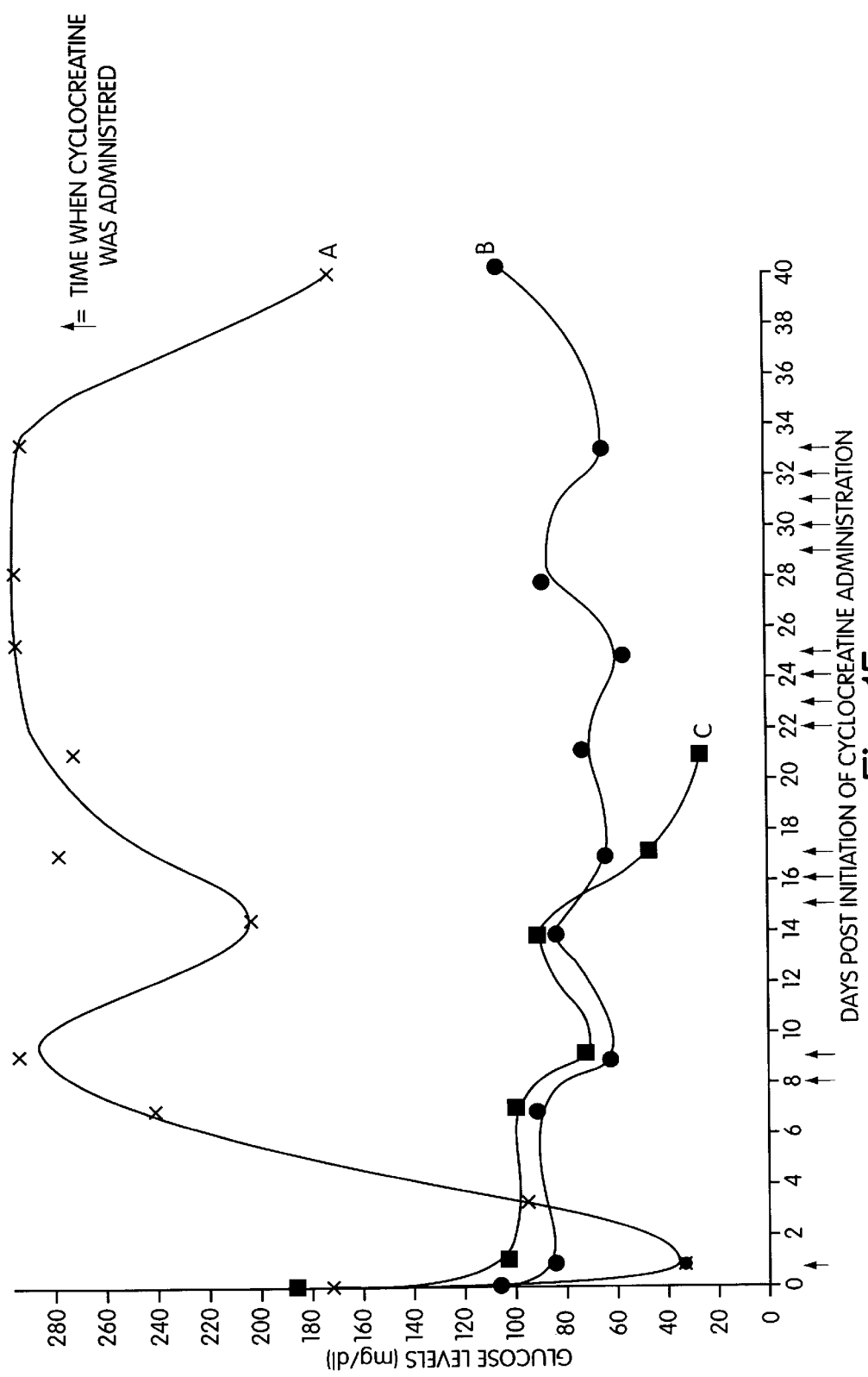
FIG. 15 graphically illustrates three individual patients' glucose levels upon treatment with cyclocreatine at a dose of 80 mg/Kg. Patients were treated with cyclocreatine via a 3 hour continuous infusion in a one liter volume of saline using the schedule of administration as described in Example 6.
Figure 16:
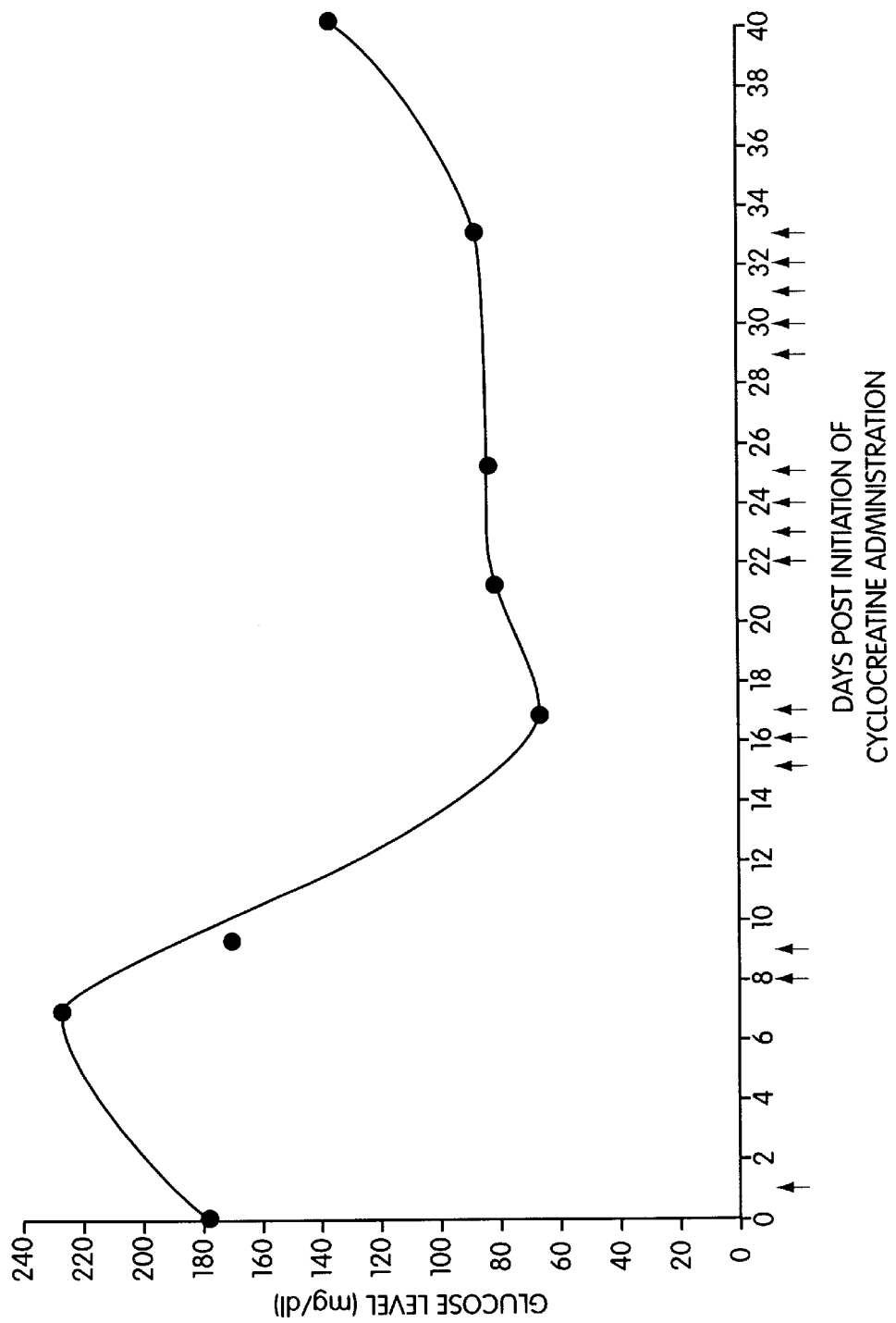
FIG. 16 graphically illustrates glucose levels in a diabetic cancer patient upon treatment with cyclocreatine at a dose of 10 mg/Kg. The patient was treated with cyclocreatine via a 3 hour continuous infusion in a one liter volume of saline using the schedule of administration as described in Example 6.

Cohorts of 3 patients were administered drug at each dose level, via a 3 hour continuous infusion in one liter volume of saline. The first week patients received cyclocreatine once, the second week patients received cyclocreatine twice, the third week three times, the fourth week four times, the fifth week five times. On weeks six and seven, no drug was administered to allow the drug to wash out. On week eight, cyclocreatine was given five times. The study included a total of 23 patients (18 male, 5 female) with a median age of 71 years (range 54–85). The patients had different types of malignancies. Eligibility requirements included patients who have failed standard therapy or for whom no therapy was available, normal organ function, have recovered from prior therapies, probability of survival of greater than three months. Reasons for exclusion included: major surgery, life threatening concurrent illness and CNS metastasis. Blood samples were collected at baseline and 1 day before and after the last weekly drug administration on days 1, 7, 9, 14, 17, 21, 25, 28, 33, 40, 47, 49, 54, 61, and 69. Glucose levels were determined for these collected blood samples. Significant hypoglycemia was noted at the highest tested drug concentrations (2 out of 3 patients treated at the 80 mg/Kg level and 2 out of 7 at the 100 mg/Kg dose). These patients became lethargic and hypoglycemic and required immediate intervention to revert glucose levels. At the lower tested drug concentrations there seemed to be a trend towards a drop in glucose levels shortly after drug administration. Not all patients experienced a significant drop in glucose although the trend was there. FIGS. 14 and 15 illustrate graphically individual patients' glucose levels upon treatment with 60 mg/Kg or 80 mg/Kg cyclocreatine. Patient (A) at the 80 mg/Kg dose was diabetic and had many serious complications due to his disease. Insulin was withdrawn in the middle of the study due to these complications and that resulted in marked increase in his glucose level. His glucose did not seem to respond well to cyclocreatine. Tables 5–10 give the raw data for glucose levels in individual patients. It should be noted that an insufficient number of readings was made shortly after drug administration. It is interesting to note that several patients who were diabetic or had higher glucose levels than normal did respond to cyclocreatine, onen example being illustrated in FIG. 16.

TABLE 5

Glucose (mg/dl) (Normal 70–150)

| | Patient | | | |
|---|---|---|---|---|
| | 11 | 12 | 13 | |
| | Dose (mg/Kg) | | | Ave |
| Study Day | 60 | 60 | 60 | 60 |
| 0 | 118 | 83 | 147 | 116 |
| 1 | 78 | 80 | 100 | 39 |
| 7 | 141 | 72 | 48 | 37 |
| 9 | 89 | 92 | | 91 |
| 14 | 108 | 105 | 93 | 102 |
| 17 | 92 | 73 | 92 | 36 |
| 21 | 90 | 138 | 82 | 103 |
| 26 | 90 | 68 | 75 | 78 |
| 28 | | 74 | 56 | 65 |
| 33 | | 113 | 85 | 99 |
| 40 | | 83 | 67 | 75 |
| 47 | | 95 | 142 | 119 |
| 49 | | 98 | 106 | 102 |
| 54 | | | 72 | 72 |
| 61 | | 106 | 64 | 85 |
| 69 | | 112 | 141 | 127 |

TABLE 6

Glucose (mg/dl) (Normal 70–150)

| | Patient | | | |
|---|---|---|---|---|
| | 14 | 15 | 16 | Ave |
| | Dose (mg/Kg) | | | |
| Study Day | 80 | 80 | 80 | 80 |
| 0 | 172 | 100 | 182 | 151 |
| 1 | 33 | 85 | 102 | 73 |
| 7 | 243 | 93 | 102 | 146 |
| 9 | 378 | 65 | 68 | 170 |
| 14 | 198 | 88 | 94 | 127 |
| 17 | 291 | 63 | 47 | 134 |
| 21 | 271 | 72 | 30 | 172 |
| 25 | 352 | 62 | | 207 |
| 28 | 364 | 89 | | 227 |
| 33 | 345 | 67 | | 206 |
| 40 | 175 | 106 | | 141 |
| 47 | | 77 | | 77 |
| 49 | 280 | 89 | | 185 |
| 54 | 416 | 87 | | 252 |
| 61 | | 81 | | 81 |
| 69 | | 81 | | 81 |

TABLE 7

Glucose (mg/dl) (Normal 70–150)

| | Patient | | | | | | | |
|---|---|---|---|---|---|---|---|---|
| | 17 | 18 | 19 | 20 | 21 | 22 | 23 | Ave |
| | Dose(mg/Kg) | | | | | | | |
| Study Day | 100 | 100 | 100 | 100 | 100 | 100 | 100 | 100 |
| 0 | 121 | 122 | 115 | 104 | 158 | 137 | 168 | 132 |
| 1 | 122 | 98 | 101 | 104 | 178 | 170 | 216 | 141 |
| 7 | 127 | 104 | 87 | 160 | 99 | 108 | 228 | 130 |
| 9 | 145 | 84 | 92 | 77 | 246 | 91 | 173 | 130 |
| 14 | 71 | 126 | | 90 | 100 | 87 | | 95 |
| 17 | 150 | 97 | | 151 | | 84 | 184 | 133 |
| 21 | 104 | 85 | 50 | 76 | | 77 | 163 | 101 |
| 25 | 102 | 80 | | 111 | | 77 | 257 | 125 |
| 28 | 125 | 71 | | 137 | | 109 | 325 | 153 |
| 33 | 136 | 119 | | 165 | | 143 | 288 | 170 |
| 40 | 162 | 109 | | 141 | | 107 | | 130 |
| 47 | 108 | 114 | | 101 | | 121 | | 111 |
| 49 | 80 | 95 | | 99 | | 119 | | 98 |
| 54 | 114 | 49 | | 91 | | 71 | | 81 |
| 61 | 122 | 80 | | | | 109 | | 104 |
| 69 | 86 | 84 | | | | 107 | | 92 |

TABLE 8

Glucose (mg/dl) (Normal 70–150)

| | Patient | | | | | | |
|---|---|---|---|---|---|---|---|
| | 1 | 2 | 3 | 2,1 | 2,2 | 2,3 | Ave |
| | Dose (mg/Kg) | | | | | | |
| Study Day | 10 | 10 | 10 | 10 | 10 | 10 | 10 |
| 0 | 180 | 122 | 121 | 99 | 108 | 109 | 123 |
| 1 | | 125 | | 78 | 84 | 138 | 119 |
| 7 | 229 | 119 | 77 | 85 | 83 | 144 | 123 |
| 9 | 170 | 115 | 116 | 83 | 118 | 109 | 119 |
| 14 | | 126 | | 81 | 126 | 105 | 110 |
| 17 | 67 | | 72 | 108 | | 84 | 83 |
| 21 | 82 | 223 | 108 | 101 | 89 | 225 | 138 |
| 25 | 82 | 141 | 96 | 100 | 93 | | 102 |
| 28 | | 59 | 70 | 103 | 90 | 97 | 84 |

TABLE 8-continued

Glucose (mg/dl) (Normal 70–150)

| | Patient | | | | | | |
|---|---|---|---|---|---|---|---|
| | 1 | 2 | 3 | 2,1 | 2,2 | 2,3 | Ave |
| | Dose (mg/Kg) | | | | | | |
| Study Day | 10 | 10 | 10 | 10 | 10 | 10 | 10 |
| 33 | 84 | 97 | 94 | 76 | 110 | 54 | 86 |
| 40 | 136 | 89 | 98 | 80 | 109 | 214 | 121 |
| 47 | 58 | 117 | 95 | 86 | | 128 | 97 |
| 49 | 147 | | | 93 | 191 | 223 | 164 |
| 54 | 160 | 103 | 85 | 107 | | 56 | 102 |
| 61 | 125 | 128 | | 100 | | 171 | 131 |
| 69 | 104 | 124 | 104 | 90 | | 335 | 151 |

TABLE 9

Glucose (mg/dl) (Normal 70–150)

| | Patient | | | | | | | |
|---|---|---|---|---|---|---|---|---|
| | 4 | 5 | 6 | 7 | 2,4 | 2,5 | 2,6 | Ave |
| | Dose (mg/Kg) | | | | | | | |
| Study Day | 20 | 20 | 20 | 20 | 20 | 20 | 20 | 20 |
| 0 | 84 | 117 | 85 | 240 | 151 | 77 | 84 | 120 |
| 1 | 77 | 91 | 83 | 201 | 232 | 96 | 121 | 129 |
| 7 | 85 | 114 | 141 | 120 | 80 | 96 | 137 | 110 |
| 9 | 79 | 84 | | 161 | | 104 | 131 | 112 |
| 14 | 93 | | | 207 | 181 | 99 | 138 | 144 |
| 17 | 60 | 89 | | 135 | | 68 | 93 | 89 |
| 21 | 73 | 136 | | 154 | 180 | 84 | 139 | 128 |
| 25 | 90 | 100 | | | | 89 | 102 | 97 |
| 28 | 88 | 180 | | 172 | | 67 | 128 | 127 |
| 33 | 70 | 89 | | 174 | | 77 | 94 | 101 |
| 40 | 74 | 121 | | 159 | | 106 | 99 | 112 |
| 47 | | | | 202 | | 86 | 99 | 129 |
| 49 | | 88 | 90 | 201 | | | | 126 |
| 54 | | 89 | 60 | 120 | | 91 | | 90 |
| 61 | | 74 | 102 | 128 | | 98 | | 101 |
| 69 | | 83 | 114 | 156 | | 77 | | 108 |

TABLE 10

Glucose (mg/dl) (Normal 70–150)

| | Patient | | | | | | |
|---|---|---|---|---|---|---|---|
| | 8 | 9 | 10 | 2,7 | 2,8 | 2,9 | Ave |
| | Dose (mg/Kg) | | | | | | |
| Study Day | 40 | 40 | 40 | 40 | 40 | 40 | 40 |
| 0 | 94 | 118 | 100 | 115 | 222 | 98 | 125 |
| 1 | 114 | 114 | | 95 | 116 | 87 | 105 |
| 7 | 96 | 78 | 156 | 153 | | 117 | 119 |
| 9 | 115 | 130 | 84 | 123 | 148 | 148 | 125 |
| 14 | 87 | 151 | 123 | 102 | 184 | 126 | 129 |
| 17 | 91 | 145 | 93 | 117 | 251 | 139 | 139 |
| 21 | 103 | 156 | 106 | 104 | | 90 | 112 |
| 25 | 96 | 210 | 143 | 122 | 278 | 114 | 161 |
| 28 | 125 | 151 | 91 | 154 | | 87 | 122 |
| 33 | 122 | 109 | | | 244 | 121 | 149 |
| 40 | 67 | 128 | 94 | | 139 | 92 | 104 |
| 47 | 116 | 75 | 100 | | | 105 | 99 |
| 49 | 122 | | | | 129 | 132 | 128 |
| 54 | 136 | 145 | 79 | | 185 | 105 | 132 |
| 61 | 102 | 121 | 92 | | | 104 | 105 |
| 69 | 135 | 89 | 74 | 205 | 92 | 119 | |

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating or preventing a glucose metabolic disorder in a subject afflicted with said disorder, comprising administering to said subject an amount of a creatine compound, or a pharmaceutically acceptable salt thereof, effective to regulate said subject's glucose level, such that treatment occurs.

2. The method of claim 1 wherein said disorder is hyperglycemia.

3. The method of claim 1 wherein said disorder is insulin dependent diabetes mellitus.

4. The method of claim 1 wherein said disorder is impaired glucose tolerance.

5. The method of claim 1 wherein said disorder is hyperinsulinemia.

6. The method of claim 1 wherein said disorder is insulin insensitivity.

7. The method of claim 1 wherein said disorder is diabetes related diseases.

8. The method of claim 1 wherein the subject is a mammal.

9. The method of claim 8 wherein the subject is a human.

10. A method for treating a metabolic disorder selected from the group consisting of hyperglycemia, insulin dependent diabetes mellitus, impaired glucose tolerance, hyperinsulinemia, insulin insensitivity, diabetes related diseases, in a subject afflicted with said disorder, comprising administering to the subject a therapeutic amount of a creatine analogue having the general formula:

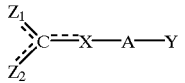

and pharmaceutically acceptable salts thereof, wherein:

a) Y is selected from the group consisting of: —$CO_2H$—NHOH, —$NO_2$, —$SO_3H$, —C(=O)$NHSO_2J$ and —P(=O)(OH)(OJ), wherein J is selected from the group consisting of: hydrogen, $C_1$–$C_6$ straight chain alkyl, $C_3$–$C_6$ branched alkyl, $C_2$–$C_6$ alkenyl, $C_3$–$C_6$ branched alkenyl, and aryl;

b) A is selected from the group consisting of: C, CH, $C_1$–$C_5$alkyl, $C_2$–$C_5$alkenyl, $C_2$–$C_5$alkynyl, and $C_1$–$C_5$alkoyl chain, each having 0–2 substituents which are selected independently from the group consisting of:

1) K, where K is selected from the group consisting of: $C_1$–$C_6$ straight alkyl, $C_2$–$C_6$ straight alkenyl, $C_1$–$C_6$ straight alkoyl, $C_3$–$C_6$ branched alkyl, $C_3$–$C_6$ branched alkenyl, and $C_4$–$C_6$ branched alkoyl, K having 0–2 substituents independently selected from the group consisting of: rromo, chloro, epoxy and acetoxy;

2) an aryl group selected from the group consisting of: a 1–2 ring carbocycle and a 1–2 ring heterocycle, wherein the aryl group contains 0–2 substituents independently selected from the group consisting of: —$CH_2L$ and —$COCH_2L$ where L is independently selected from the group consisting of: bromo, chloro, epoxy and acetoxy; and 3) —NH—M, wherein M is selected from the group consisting of: hydrogen, $C_1$–$C_4$ alkyl, $C_2$–$C_4$ alkenyl, $C_1$–$C_4$ alkoyl, $C_3$–$C_4$ branched alkyl, $C_3$–$C_4$ branched alkenyl, and $C_4$ branched alkoyl;

c) X is selected from the group consisting of $NR_1$, $CHR_1$, $CR_1$, O and S, wherein $R_1$ is selected from the group consisting of:
1) hydrogen;
2) K where K is selected from the group consisting of: $C_1$–$C_6$ straight alkyl. $C_2$–$C_6$ straight alkenyl, $C_1$–$C_6$ straight alkoyl, $C_3$–$C_6$ branched alkyl, $C_3$–$C_6$ branched alkenyl, and $C_4$–$C_6$ branched alkoyl, K having 0–2 substituents independently selected from the group consisting of: bromo, chloro, epoxy and acetoxy;
3) an aryl group selected from the group consisting of a 1–2 ring carbocycle and a 1–2 ring heterocycle, wherein the aryl group contains 0–2 substituents independently selected from the group consisting of: —$CH_2L$ and —$COCH_2L$ where L is independently selected from the group consisting of: bromo, chloro, epoxy and acetoxy;
4) a $C_5$–$C_9$ a-amino-w-methyl-w-adenosylcarboxylic acid attached via the w-methyl carbon;
5) 2 $C_5$–$C_9$ a-amino-w-aza-w-methyl-w-adenosylcarboxylic acid attached via the w-methyl carbon; and
6) a $C_5$–$C_9$ a-amino-w-thia-w-methyl-w-adenosylcarboxylic acid attached via the w-methyl carbon;

d) $Z_1$ and $Z_2$ are chosen independently from the group consisting of: =O, —$NHR_2$, —$CH_2R_2$, —$NR_2OH$; wherein $Z_1$ and $Z_2$ may not both be =O and wherein $R_2$ is selected from the group consisting of:
1) hydrogen;
2) K, where K is selected from the group consisting of: $C_1$–$C_6$ straight alkyl; $C_2$–$C_6$ straight alkenyl, $C_1$–$C_6$ straight alkoyl, $C_3$–$C_6$ branched alkyl, $C_3$–$C_6$ branched alkenyl, and $C_4$–$C_6$ branched alkoyl, K having 0–2 substituents independently selected from the group consisting of: bromo, chloro, epoxy and acetoxy;
3) an aryl group selected from the group consisting of a 1–2 ring carbocycle and a 1–2 ring heterocycle, wherein the aryl group contains 0–2 substituents independently selected from the group consisting of: —$CH_2L$ and —$COCH_2L$ where L is independently selected from the group consisting of: bromo, chloro, epoxy and acetoxy;
4) 2 $C_4$–$C_8$ a-amino-carboxylic acid attached via the w-carbon;
5) B, wherein B is selected from the group consisting of: —$CO_2H$—NHOH, —$SO_3H$, —$NO_2$, OP(=O)(OH)(OJ) and —P(=O)(OH)(OJ), wherein J is selected from the group consisting of: hydrogen, $C_1$–$C_6$ straight alkyl, $C_3$–$C_6$ branched alkyl, $C_2$–$C_6$ alkenyl, $C_3$–$C_6$ branched alkenyl, and aryl, wherein B is optionally connected to the nitrogen via a linker selected from the group consisting of: $C_1$–$C_2$ alkyl, $C_2$ alkenyl, and $C_1$–$C_2$ alkoyl;
6) —D—E, wherein D is selected from the group consisting of: $C_1$–$C_3$ straight alkyl, $C_3$ branched alkyl, $C_2$–$C_3$ straight alkenyl, $C_3$ branched alkenyl, $C_1$–$C_3$ straight alkoyl, aryl and aroyl; and E is selected from the group consisting of: —$(PO_3)_n$NMP, where n is 0–2 and NMP is ribonucleotide monophosphate connected via the 5'-phosphate, 3'-phosphate or the aromatic ring of the base; —[P(=O)($OCH_3$)(O)]$_m$—Q, where m is 0–3 and Q is a ribonucleoside connected via the ribose or the aromatic ring of the base; —[P(=O)(OH)($CH_2$)]$_m$—Q, where m is 0–3 and Q is a ribonucleoside connected via the ribose or the aromatic ring of the base; and an aryl group containing 0–3 substituents chosen independently from the group consisting of: Cl, Br, epoxy, acetoxy, —OG, —C(=O)G, and —$CO_2G$, where G is independently selected from the group consisting of: $C_1$–$C_6$ straight alkyl, $C_2$–$C_6$ straight alkenyl, $C_1$–$C_6$ straight alkoyl, $C_3$–$C_6$ branched alkyl, $C_3$–$C_6$ branched alkenyl, $C_4$–$C_6$ branched alkoyl, wherein E may be attached to any point to D, and if D is alkyl or alkenyl, D may be connected at either or both ends by an amide linkage; and
7) —E, wherein E is selected from the group consisting of —$(PO_3)_n$NMP, where n is 0–2 and NMP is a ribonucleotide monophosphate connected via the 5'-phosphate, 3'-phosphate or the aromatic ring of the base; —[P(=O)($OCH_3$)(O)]$_m$—Q, where m is 0–3 and Q is a ribonucleoside connected via the ribose or the aromatic ring of the base; —[P(=O)(OH)($CH_2$)]$_m$—Q, where m is 0–3 and Q is a ribonucleoside connected via the ribose or the aromatic ring of the base; and an aryl group containing 0–3 substituents chose independently from the group consisting of: Cl, Br, epoxy, acetoxy, —OG, —C(=O)G, and —$CO_2G$, where G is independently selected from the group consisting of: $C_1$–$C_6$ straight alkyl, $C_2$–$C_6$ straight alkenyl, $C_1$–$C_6$ straight alkoyl, $C_3$–$C_6$ branched alkyl, $C_3$–$C_6$ branched alkenyl, $C_4$–$C_6$ branched alkoyl; and if E is aryl, E may be connected by an amide linkage;

e) if $R_1$ and at least one $R_2$ group are present, $R_1$ may be connected by a single or double bond to an $R_2$ group to form a cycle of 5 to 7 members;

f) if two $R_2$ groups are present, they may be connected by a single or a double bond to form a cycle of 4 to 7 members; and g) if $R_1$ is present and $Z_1$ or $Z_2$ is selected from the group consisting of —$NHR_1$, —$CH_2R_2$ and —$NR_2OH$, then $R_1$ may be connected by a single or double bond to the carbon or nitrogen of either $Z_1$ or $Z_2$ to form a cycle of 4 to 7 members.

11. The method of claim 10 wherein the creatine compound is administered in combination with insulin or a sulphonylurea compound.

12. The method of claim 10 wherein the creatine compound is cyclocreatine.

13. The method of claim 10 wherein the creatine compound is creatine phosphate.

14. A method for treating a metabolic disorder selected from the group consisting of hyperglycemia, insulin dependent diabetes mellitus, impaired glucose tolerance, hyperinsulinemia, insulin insensitivity, diabetes related diseases, in a subject afflicted with said disorder comprising administering to the subject an effective therapeutic amount of a substrate of creatine kinase, wherein said effective therapeutic amount is effective to regulate said subject's glucose level, such that treatment occurs.

15. A method for treating a glucose metabolic disorder selected from the group consisting of hyperglycemia, insulin dependent diabetes mellitus, impaired glucose tolerance, hyperinsulinemia, insulin insensitivity, diabetes related diseases in a subject afflicted with said disorder comprising administering to the subject an effective therapeutic amount of a creatine phosphate analogue.

* * * * *